(12) United States Patent
Spencer et al.

(10) Patent No.: US 6,531,107 B1
(45) Date of Patent: Mar. 11, 2003

(54) FABRICATION OF MOLECULAR NANOSYSTEMS

(75) Inventors: James T. Spencer, Fayetteville, NY (US); Damian G. Allis, Syracuse, NY (US)

(73) Assignee: Syracuse University, Syracuse, NY (US)

( * ) Notice: Subject to any disclaimer, the term of this patent is extended or adjusted under 35 U.S.C. 154(b) by 0 days.

(21) Appl. No.: 09/679,929

(22) Filed: Oct. 5, 2000

Related U.S. Application Data
(60) Provisional application No. 60/159,301, filed on Oct. 14, 1999.

(51) Int. Cl.⁷ .......................... C01B 35/00; C01B 35/18; C07F 5/02
(52) U.S. Cl. .......................... 423/276; 423/659; 556/46; 556/136; 556/140; 568/1; 568/3; 568/4; 585/24; 585/25; 585/26; 585/350; 585/352
(58) Field of Search ................................ 423/276, 659; 556/136, 140, 46; 568/1, 3, 4; 585/24, 25, 26, 350, 352

(56) References Cited

PUBLICATIONS

Achim Müller et al, Giant Ring–Shaped Building Blocks Linked to Form a Layered Cluster Network with Nanosized Channels: $[Mo_{124}^{VI} Mo_{28}^V O_{429} (M_3–O)_{28} H_{14} (H_2O)_{66.5}]^{16-}$, *Chem. Eur. J.* (1999), 5 (5), 1496–1502.*

Xiangsheng Meng et al, "Metallacarborane Staircase Oligomers. Stepwise Assembly via Tetradecker Stacking Reactions," *J. Am. Chem. Soc.* (1993), 115 (14), 6143–51 (no month).*

Xiaatai Wang et al, "Organotransition—Metal Metallacarboranes. 44. Construction of Pentadecker and Hexadecker Sandwiches from Triple–Decker Building Blocks," *J. Am. Chem. Soc.* (1995), 117(49), 1227–34 (no month).*

\* cited by examiner

*Primary Examiner*—Wayne A. Langel
(74) *Attorney, Agent, or Firm*—Wall Marjama & Bilinski LLP

(57) ABSTRACT

The invention relates to structural subunits called "synthons" which are suitable for use in the design and manufacture of molecular nanostructures, machines, and devices.

The synthon comprises polyhedra units and other species which exhibit rigid structural frameworks, the availability of stereo- and regiochemically directed substitution patterns, synthetic availability and accessability with substitutional control, diversity of available structural arrangements with said polyhedra units and related species, and connecting means which function to join adjacent synthons.

8 Claims, 20 Drawing Sheets

} to "V"

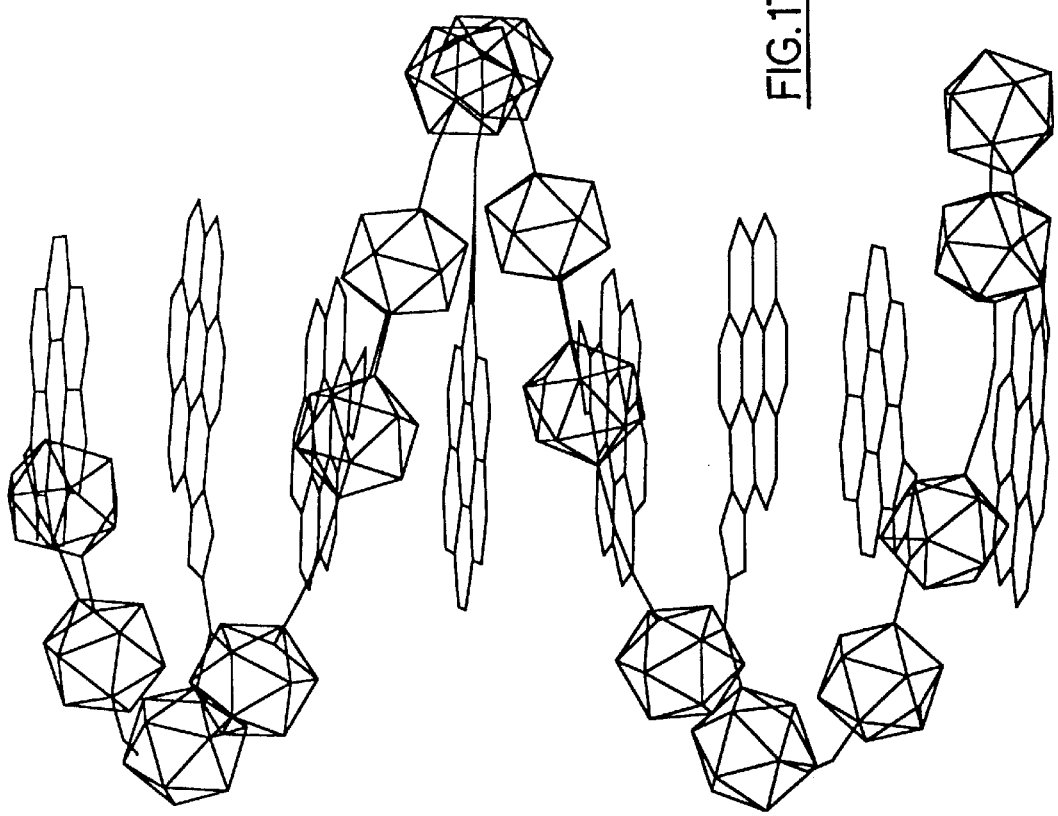
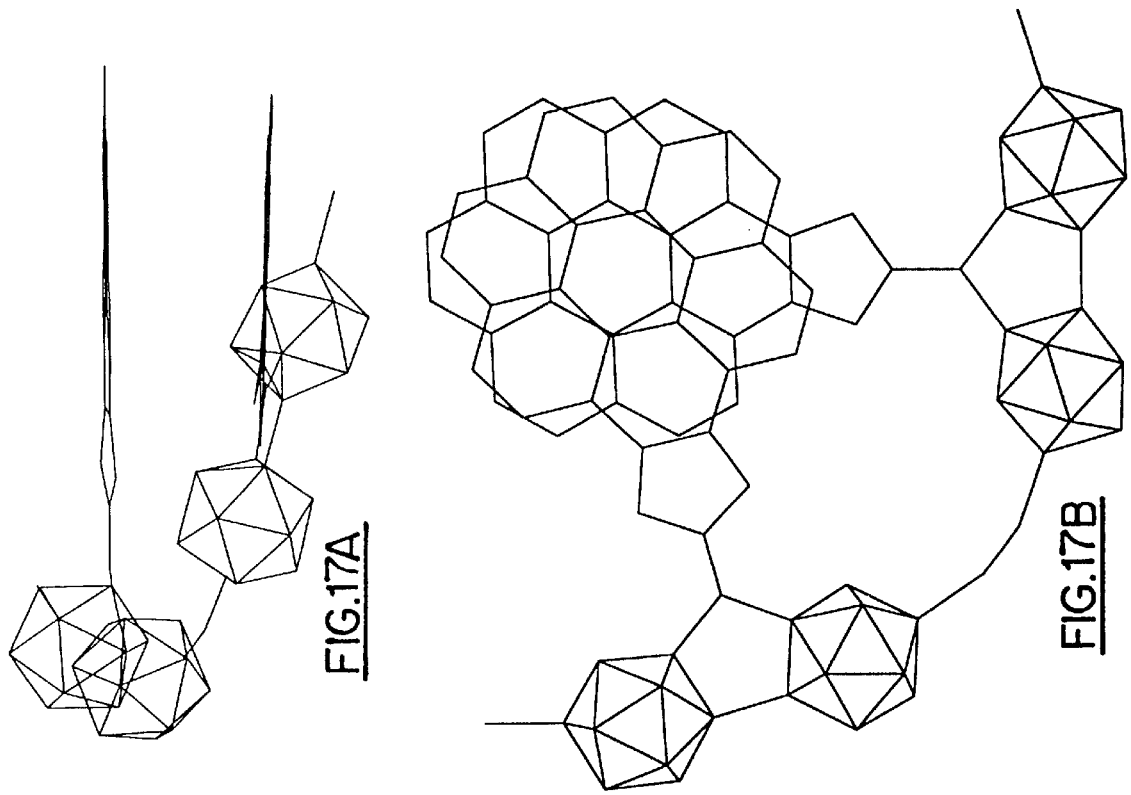

FABRICATION OF MOLECULAR NANOSYSTEMS

This application claims benefit of provisional application No. 60/159,301 filed Oct. 14, 1999.

FIELD OF THE INVENTION

This invention relates generally to nanoscale molecular assemblies and, more specifically, to the use of structural subunits called "synthons" in the design and manufacture of molecular macrostructures, machines, and devices.

BACKGROUND OF THE INVENTION

The invention relates to molecular assemblies at the nanoscale, commonly referred to as nanosystems, and, more specifically, to macromolecular nanostructures and advanced materials using a design motif based on the application of main group and transition metal polyhedral clusters as rigid components in the design of structural subunits for the construction of nanoscale molecular assemblies.

Recent years have witnessed truly remarkable achievements in many fields of science and technology. Among these, advances in the areas of new materials and macromolecules with designed features have been particularly dramatic. Theoreticians are now seriously proposing the cognizant design and unidirectional fabrication of atomic and molecular assemblies on the nanometer scale with atomic precision (1). The design and construction of large-scale molecular arrays is clearly the enabling science for the realization of the proposed potential of nanotechnology. While it is expected that the realization of this potential may be far in the future, the proposed structures and molecular assemblies are currently serving as goals for both theoretical and experimental studies. Along the way, many of the smaller molecules and assemblies intermediate in the fabrication of these and other proposed larger structures are fully expected, in their own right, to provide immediate and significant advances in a variety of areas, including macromolecular design and construction, optoelectronic applications, medicine, and new advanced materials.

Chemists have long been involved with the design and synthesis of functionalized molecules with specific structural, chemical, and physical properties. Few of these studies, however, have focused on the use of molecular functionalization as a means to the directional design of structural building elements for the fabrication of larger mechanical and rigid structures at the nanoscale. Studies toward this focus have recently been pursued by the consideration of large atomic assemblies for a variety of both chemical and mechanical applications. Various terms, including nanosystems and nanoscale materials, have been used to describe this emerging field.

Most of the work thus far in nanoscale design has employed carbon as the primary structural element. Diamondoid structures, diamond thin films, and aromatic hydrocarbons (buckminsterfullerenes or, more commonly, "bucky" species) are receiving a great deal of attention due to their chemical and physical properties and, in the case of "bucky" systems, the ease of synthesis (though this ease does not currently correlate well with either the control or specificity of "bucky" synthesis). In stark contrast, boron-based materials, and main group and transition metal polyhedral cluster species in general, have been comparatively neglected as potential alternatives to these organic materials, which, in many ways, have received significant attention because of the familiarity of carbon and organic molecules in general to current nanoscale theorists actively designing macromolecules and nanosystems. Of special interest are the polyhedral boron cluster systems, one of the primary topics of this document, due to their unique chemical, physical, and synthetic properties.

For a very long time, philosophers and scientists have been fascinated by the intrinsic beauty and three dimensional shapes of polyhedra (many-faced solids). Since the work of Plato and Archimedes, philosophers, mathematicians, and, most recently, physical scientists have focused their attention on these intriguing polyhedral bodies. It is the field of main group cluster chemistry that most closely ties together the abstract, mathematical study of these pure polyhedra with the real physical and chemical world. In particular, main group cluster chemistry may be thought of as the "missing link" between small molecule behavior, with more localized bonding, and that of extended arrays and macromolecular assemblies, with extensively delocalized electronic structures. It is believed that the design and fabrication of many of the new three dimensional nanoscale molecular architectures currently being proposed and developed in the pursuit of viable molecule-based nanosystem construction may best be accomplished, in part, through the use of these polyhedral and related building blocks.

Main group clusters have presented considerable challenges to synthetic, structural, and theoretical chemists since their discovery nearly ninety years ago. The quest for a detailed understanding of these polyhedral species has led to an understanding of some very remarkable chemistry. Boron-based polyhedral structures display a number of unique chemical, physical, and structural properties that may make them particularly suitable for the fabrication of complex molecular architectures. When viewed from either a nanoscale macrostructural or materials perspective, these polyhedral cluster compounds and assemblies provide extraordinary structures with an anticipated array of unique properties, such as high stabilities, high degrees of systemic interconnection through the potential for extensive three-dimensional bonding, and high-strength molecular architectures.

With the remarkable geometric and bonding properties of these cluster species comes the flexibility of either treating each main group or transition metal cluster as a design unit in its own right or using each cluster as part of some larger synthetic subunit for the design of larger systems based on the construction limitations imposed by the new, larger subunit. The route proposed here for the construction of these remarkable structures and compounds is via the design and synthesis of smaller, structurally simple synthon elements for the subsequent design of larger macromolecular assemblies. These structures, along with proposed synthetic pathways and potential short-term applications, are described in the following sections of this document.

BRIEF DESCRIPTION OF THE DRAWING

For a fuller understanding of the nature and objects of the invention, reference should be made to the following detailed description of a preferred mode of practicing the invention, read in connection with the accompanying drawings, in which:

FIGS. 17a–b depict the idealized helical stacking structure of the linked synthons presented in FIG. 16 as determined by chemical computational methods. FIG. 17c present a optimized helical structure.

SUMMARY AND DETAILED DESCRIPTION OF THE INVENTION

Figure 1:
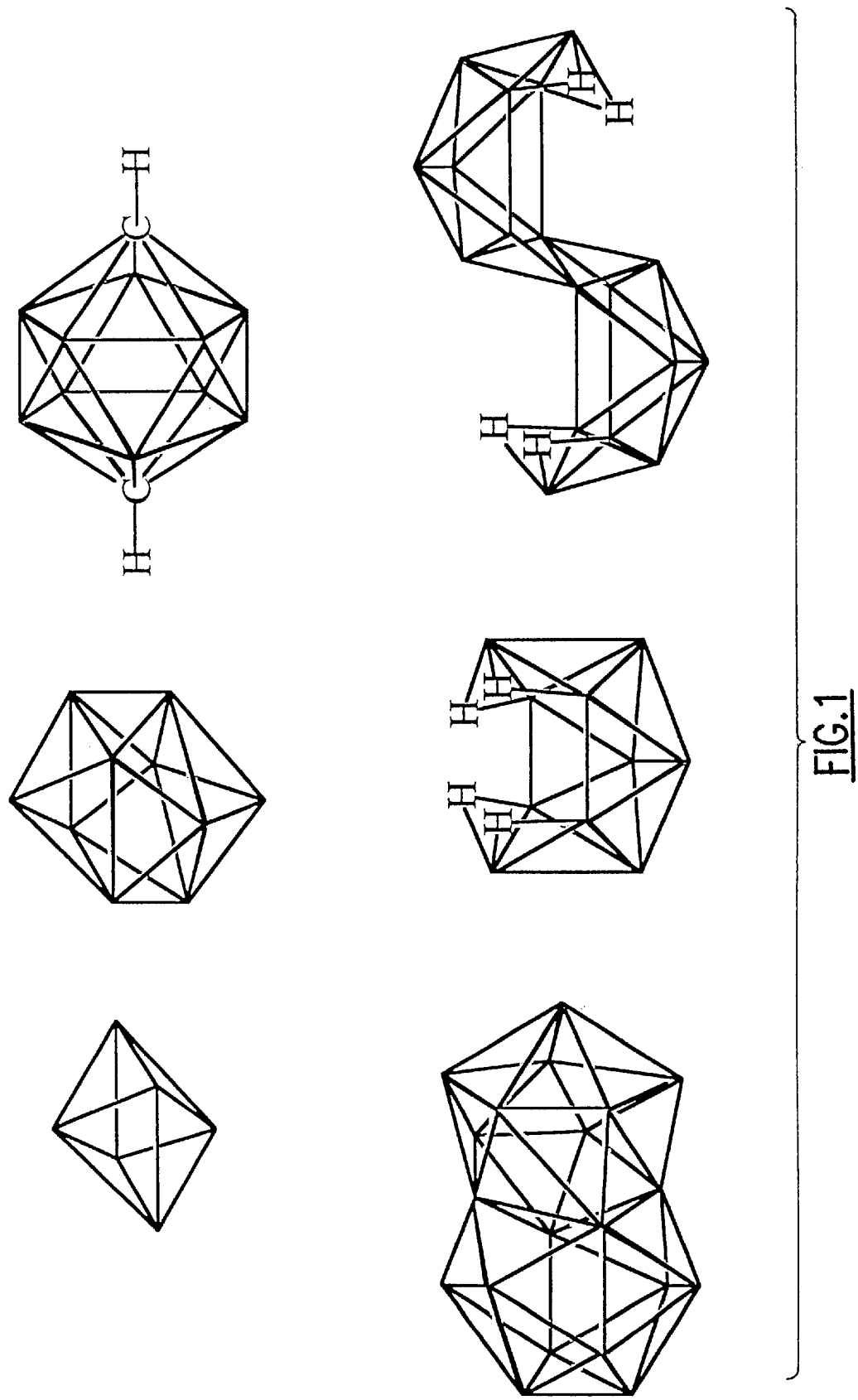
FIG. 1 represents a small selection of available boron clusters for use in the present invention.

It is therefore an object of the present invention to provide a construction approach for the design and synthesis of nanosystems.

It is another object of the present invention to provide structural subunits called "synthons" which are suitable for use in the design and manufacture of molecular macrostructures, machines, and devices.

It is another object of the present invention to provide for the design and synthesis of nanosystems based on the utilization of molecular subunits.

It is yet another object of the present invention to provide for the construction of nanosystems based on a synthetic subunit which exhibits rigid structural frameworks and directional substitution patterns.

Main group and transition metal polyhedral clusters and related species provide a unique entry into novel molecular-based materials design for the unidirectional synthesis of a variety of interesting nanoscale molecular systems. These molecular polyhedra have several distinct advantages for the fabrication of larger structures primarily arising from; (1) their rigid structural frameworks, (2) the availability of stereo- and regiochemically-directed substitution patterns, (3) their synthetic availability and accessibility (with substitutional control), (4) the diversity of available structural arrangements, (5) the extreme chemical and thermal stability of the polyhedral units, (6) their potential for designing three-dimensional arrays with atomic precision, (7) their stability to photochemical and neutron irradiation, and (8) the control of the chemical and electronic properties of the products.

Among those features of main group polyhedra mentioned above, three in particular make them especially attractive for nanostructural fabrication. These are their stability, electronic properties, and three dimensional structures. The closo-boranes and closo-carboranes, for example, exhibit exceptional thermal and chemical stability. One of the polyhedra employed here in the design of nanostructural subunits is the closo-$C_2B_{10}H_{12}$ framework, which is thermally stable to well over 600° C., is resistant to attack by boiling water, and is unreactive with oxidizing agents, reducing agents, or mineral acids. Larger, linked-$C_2B_{10}H_{12}$-based polymeric species have even shown thermal stability to long exposures at 1000° C. (2). Part of this unique stability lies in the aromatic electron delocalization within the cluster framework (3–5). Molecular orbital descriptions of the bonding in these clusters bears close resemblance to the three-dimensional benzenoid-like aromatic structure (5), a description further substantiated by the response of these species to chemical reactions commonly employed in the organic chemistry of aromatic compounds.

These borane and carborane clusters are also typically very photochemically robust due, in part, to the high connectivity of cage atoms and strong intra-cage bonding, effectively preventing atomic loss. The boron containing materials, due to both their very high thermal and high energy (104–106 eV) neutron capture cross sections ($^{10}$B[n,] 3836 Barns, 760 Barns for natural $^{11}$B), have also been employed and continue to have great potential as neutron shields and in related "nuclear-hardened" electronic and structural applications. The neutron capture cross section of boron is larger than that of all of the naturally occurring elements by orders of magnitude (5). In addition, the products from the reactions of neutrons with boron are all stable, non-radioactive species.

Main group clusters display an incredible range of three dimensional structures, including species of exceptionally high symmetry, as illustrated by a few examples for the borane and carborane species shown in FIG. 1 (6), where terminal cage hydrogens have been omitted and cage boron atoms are shown as unlabeled vertices. These polyhedral frameworks (both those shown in FIG. 1 and those well known in the literature) (6) display a unique range of structures with precise chemical control. The geometric diversity and substitutional control of these structures essentially allow for the unlimited architectural design of larger assemblies that are built upon these smaller subunits.

The difficulty in using only main group or transition metal cluster complexes for nanostructural design is that the specificity of atom or cluster placement is lost with the very statistical method of chemical synthesis. Whereas a single point on a large molecule can be functionalized by a variety of available chemical methods, the ability to control the precise arrangement and bonding of such small molecules into rigid or mechanical structures is still beyond the abilities of modern chemistry or nanostructural engineering. It is this current difficulty in nanoscale design that leads to the consideration of larger synthetic subunits with control enough to design larger-scale structures for the directed design and construction of mechanostructural nanosystems of varying shapes, sizes, and possible applications.

Polyhedral and Related Building Block Approach to Nanoscale Materials. Numerous creative and theoretically possible nanoscale macrostructural "compounds" have been proposed in the literature. The possible formation of these structures has thus far been principally discussed by building up complex structures in an atom-by-atom fashion. This approach, conceptually similar to constructing a building from sand and sawdust as starting materials, both has not yielded and likely will not yield any viable synthetic routes to these proposed macrostructures in the near future, due to the current limitations of "state of the art" approaches to macromolecular design, where fortuitous macrostructural formation is still based on statistical arguments and not on the truly directed construction of nanostructures from conscious atomistic approaches. Instead, it seems logical that the most likely early pathways to these complex macrostructural materials will be derived through synthetic chemical schemes employing "prefabricated" structural elements which can be precisely assembled into more complex nanoscale systems. While this approach will not provide the level of control or selectivity of properties that a controlled atom-by-atom construction methodology will, it will provide the groundwork by which design and construction enhancements can be gauged by nanostructural engineers with respect to the abilities of the practicing synthetic chemist. Thus, the first real synthetic challenges will be to chemically, not mechanically, build these "prefabricated" structural elements.

Our approach to the formation of complex macrostructural materials is, therefore, to begin with chemically "prefabricated" subunits with designed structural features which meet a set of carefully predetermined criteria. These criteria for subunit design include; (a) a requirement for unidirectional chemical synthesis in the construction of larger structures (i.e., only one way in which the subunits may come together to form the larger structure by employing techniques such as kinetic, thermodynamic, or steric blocking), (b) the use of rigid components with controllable structural, electronic, and chemical properties, (c) the potential for synthetically viable (very high yield) subunit preparation based upon known chemical precedent reactions from readily obtainable starting materials, and (d) the availability of adjustable chemical and structural parameters which will allow for the tailoring of subunit properties, leading to precise control in subsequent macrostructural assembly.

Our initial goals in this subunit design and fabrication are, therefore: (1) to design and prepare simpler structural subunits built of polyhedral cages and related rigid chemical structures using straightforward synthetic procedures, (2) to synthesize ring, rod, and helical larger building blocks of various geometries with interesting chemical, structural, and physical properties based upon these smaller subunits, and (3) to use these building blocks to prepare larger macrostructural assemblies. Our approach to achieving these goals is summarized in the following sections.

Figure 2:
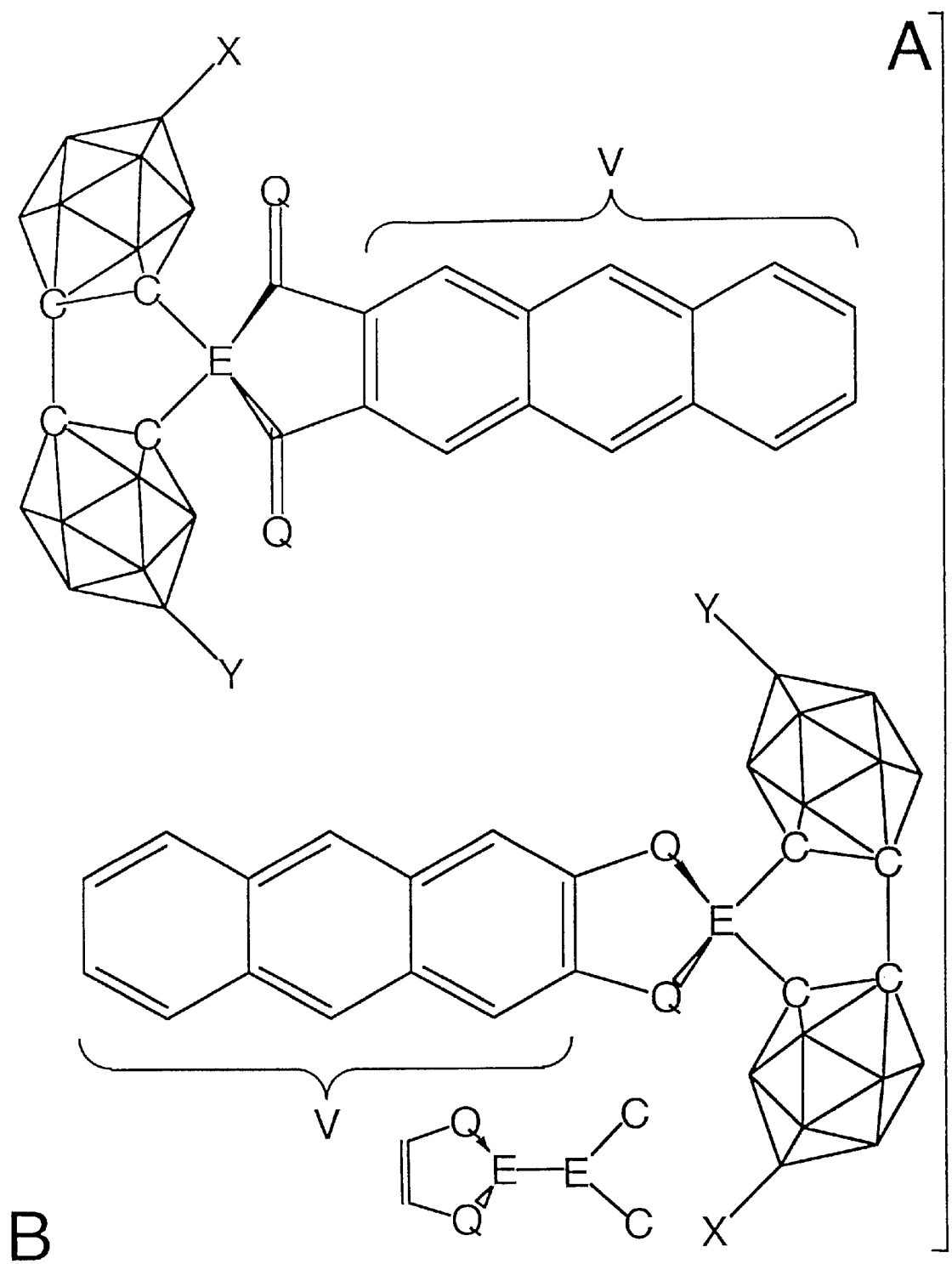
FIG. 2 represents two variations on the idealized synthon contemplated for use in the present invention.
Figure 3:
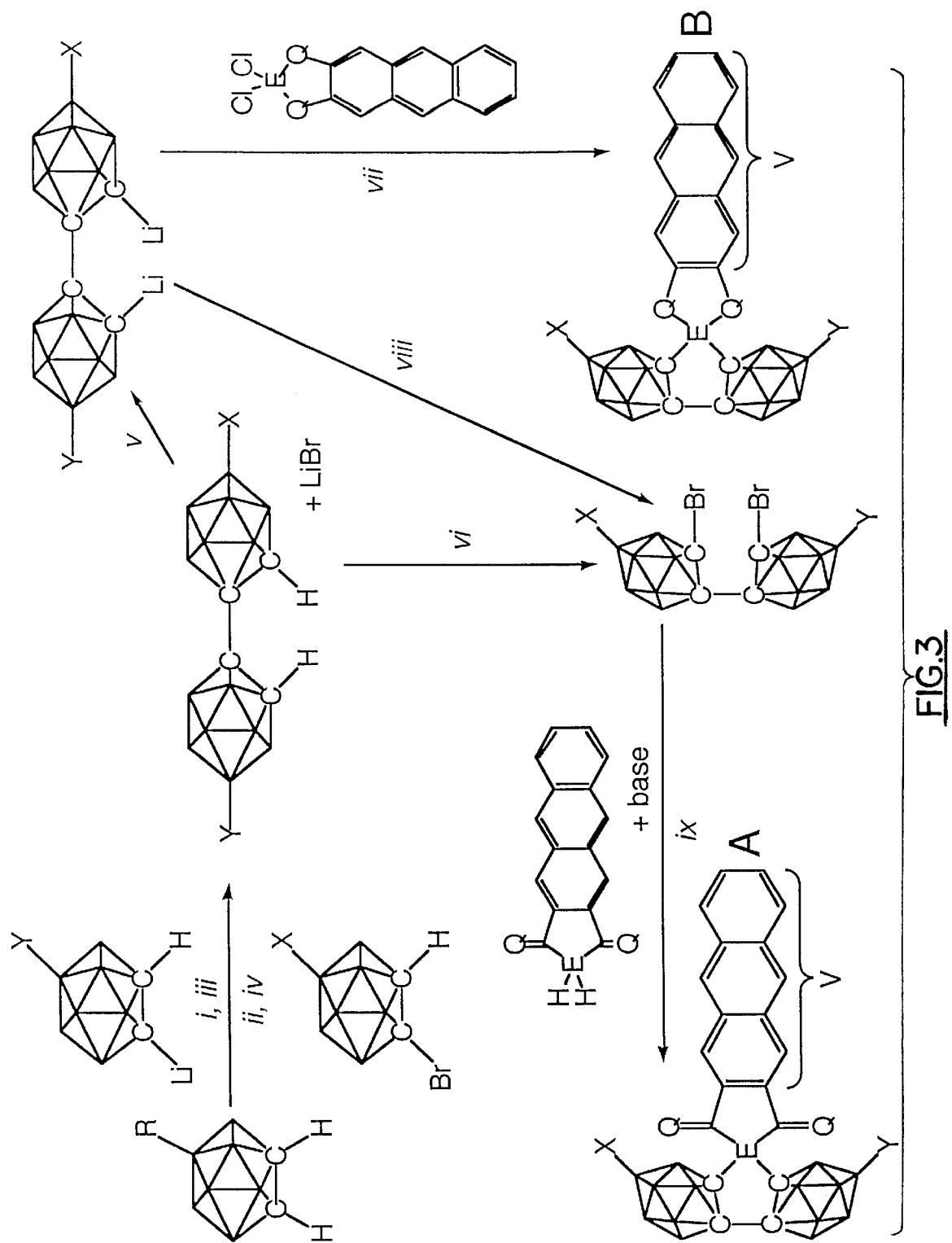
FIG. 3 represents a generalized synthetic scheme for the synthesis of various synthons.
Figure 4:
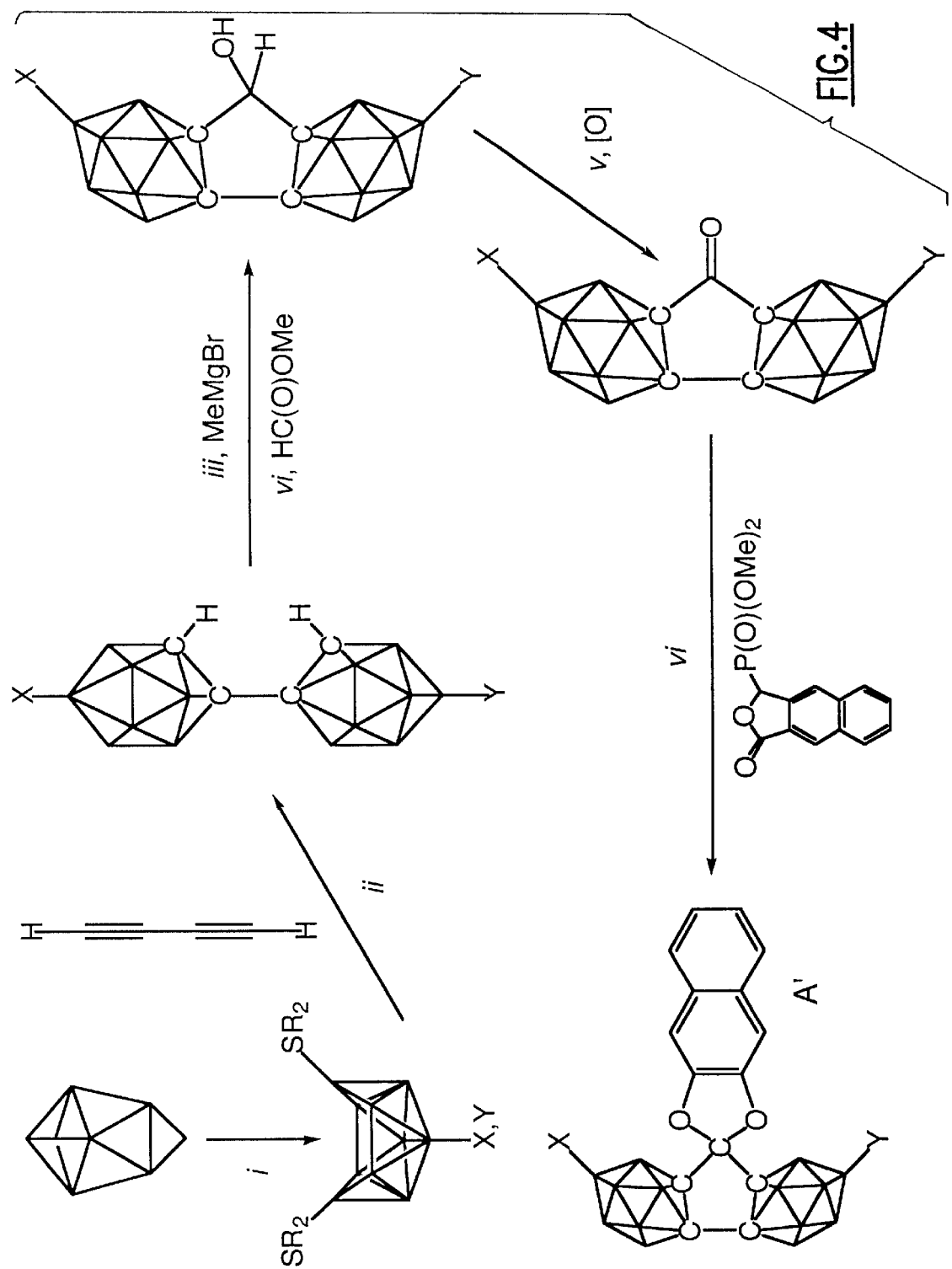
FIG. 4 represents a specific example of a synthetic approach for the synthesis of a synthon.
Figure 5A:
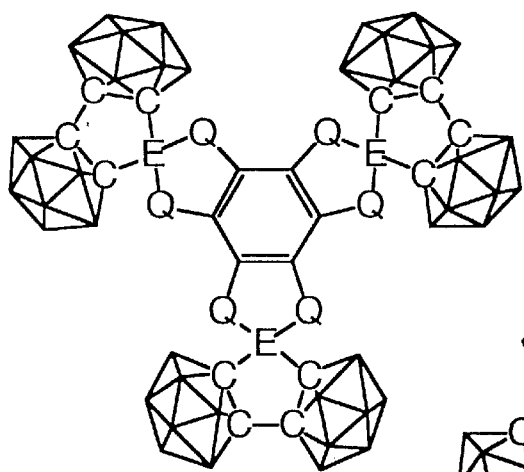
FIGS. 5a–c represents 3 specific examples of bis-cluster species for use in nanoscale construction.
Figure 5C:
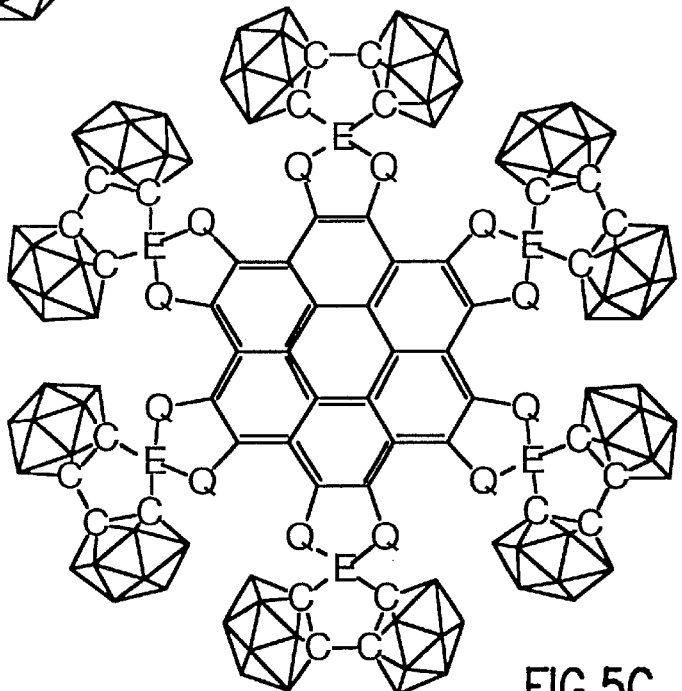
Figure 5B:
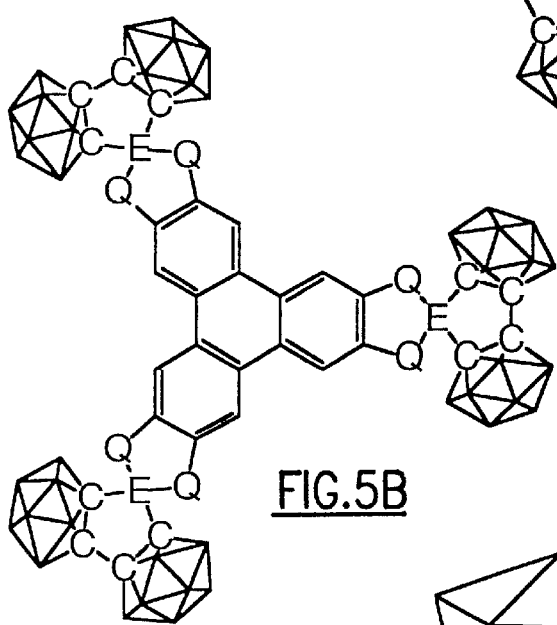
Figure 5D:
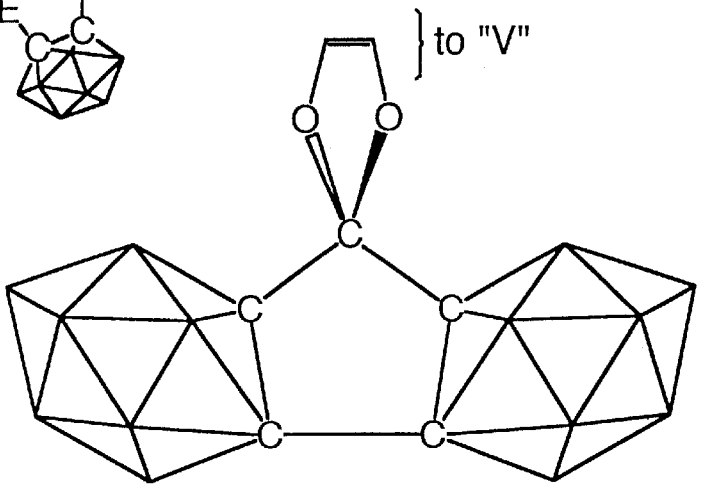
FIG. 5d demonstrates the specific linkage for the 3 species shown in FIGS. a–c.
Figure 6A:
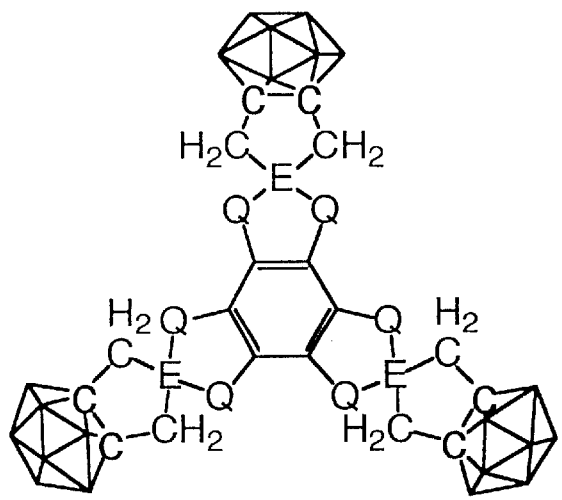
FIGS. 6a–c represents 3 specific examples of mono-cluster species for use in nanoscale construction.
Figure 6B:
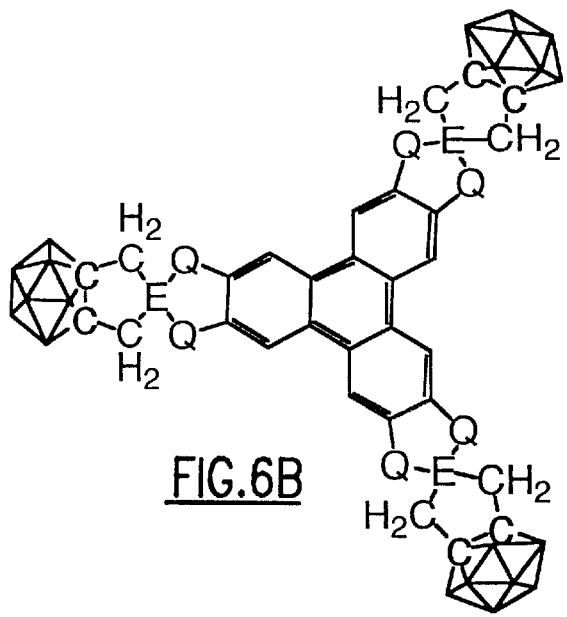
Figure 6C:
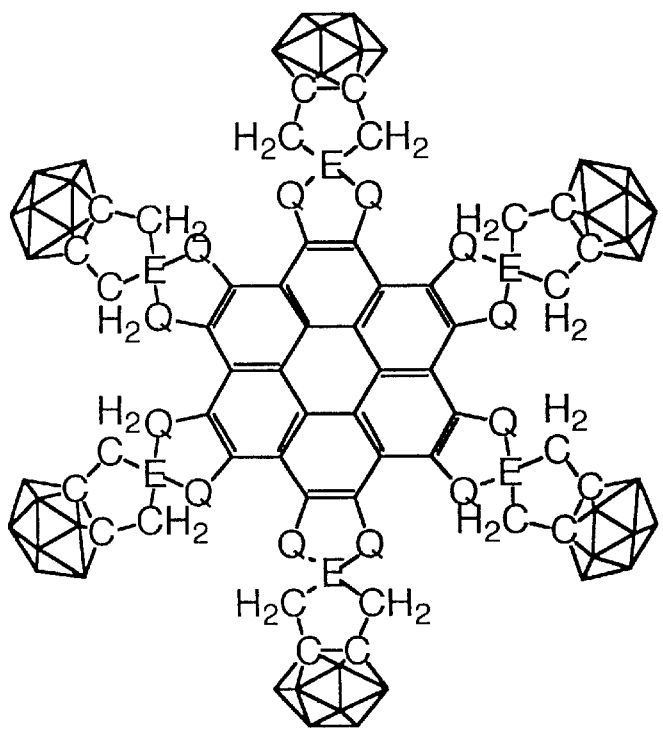
Figure 6D:
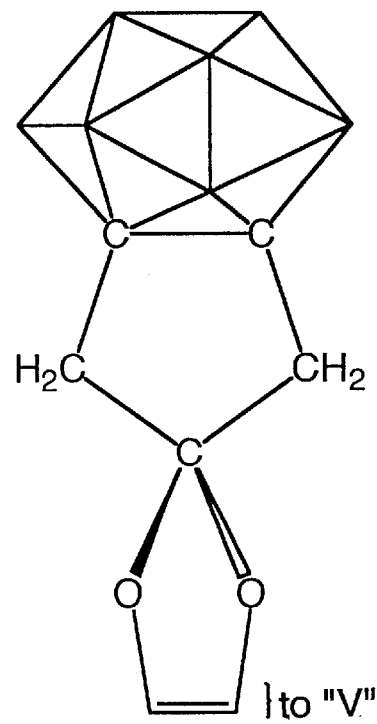
FIG. 6d demonstrates the specific linkage for the 3 species shown in FIGS. a–c.

Subunit Design and Synthesis. In our work, we have identified a number of subunits which meet the criteria set forth above. Several subunits, however, not only meet these criteria, but also display other important features which will significantly aid in macrostructural assembly, such as rigid planarity of the subunits and structural variability of the synthetic assemblies, allowing for the addition of chemical direction for the secondary structure of the nanosystem by way of such noncovalent interactions as π-arene stacking and dipolar bonding, etc., to form essentially "strain-free" macrostructures. Two variations on the design of our idealized synthon, a smaller "building block" structure based upon polyhedral units for use in nanostructural engineering, along with several proposed synthetic routes, are shown in FIGS. 2 through 4 (in all cases, unlabeled cluster vertices are boron-hydrogen bonds). In FIG. 2, the proposed synthons are based upon the ortho-$C_2B_{10}H_{12}$ structure, where Q and E (variable groups used here and throughout the reminder of the diagrams of this document) are any atoms or molecular fragments capable of coordination or bonding in the manner shown, both by three-coordinate or four-coordinate linkages, the structural minimum and maximum values for the synthon being shown. The V in FIG. 2, a convention implemented throughout the remainder of the diagrams in this document, refers to the variability of molecular fragments capable of performing a function consistent with the requirements of the application for which the synthon and, more specifically, the variable group V, is selected. As commonly implemented in the accompanying diagrams, this variable group V will be an aromatic π-system, although most any other molecular fragments capable of having a function in the design of the molecular nanosystems described are applicable. In FIG. 3, the syntheses of synthons A and B are demonstrated utilizing the ortho-$C_2B_{10}H_{12}$ cluster, where steps (i–ix) are any of a variety of possible chemical reactions needed to complete the described step in the synthetic process for the synthon. In FIG. 4, an alternate synthesis of a specific derivatization of a synthon A analog, A', is shown utilizing the nido-decaborane(14) structure, $B_{10}H_{14}$ (DIBAL-H=diiodobutylaluminum hydride and PDC=pyridinium dichromate), where steps (i–vi) are any of a variety of possible chemical reactions needed to complete the described step in the synthetic process for the synthon and step vi, by example, specifically relates to a sequence of chemical reactions where the molecule under step vi is reacted with the synthon component from step v, followed by reactions with $Me_3SiNSiMe_3Li$, DIBAL-H, and, finally, PDC. All of the synthetic reactions proposed are based upon established precedent in the literature. The framework cluster units for initial consideration are based upon the ortho-$C_2B_{10}H_{12}$ structural unit because of the well known and experimentally straightforward synthetic chemistry (with detailed substitutional control) associated with this cage species. Other frameworks besides the ortho-$C_2B_{10}H_{12}$ cluster unit may be equally well employed (i.e., meta-$C_2B_{10}H_{12}$, para-$C_2B_{10}H_{12}$, $B_{10}H_{10}^{-2}$, $B_{12}H_{12}^{-2}$, $B_{18}H_{22}$, $C_2B_8H_{10}$, $C_4B_8H_{12}$, etc.) which provide systematic variation of the structural and electronic parameters in the corresponding synthons. Several examples built upon other frameworks will be described later. Finally, the two synthons shown in FIG. 3 are derivatized at the 2 and 2' positions of the bis-cluster units (the two carbon atoms exo- to the bis-cluster bond) with pendant anthracene units connected by some linkage labeled E. It is also possible for derivatization to be accomplished at other cage sites and for other arene and related pendent groups to be employed, again providing for a large range of structural variability while maintaining precise structural and chemical control of both the primary and secondary structures of the constructed nanosystems (vide infra).

We have now successfully completed the high yield synthesis of the key ring closed intermediate [$(C_2H_{10}H_{10})_2CH(OH)$] using the pathway shown in FIG. 3. The X-ray crystal structure of this intermediate shows very close agreement between the calculated (MOPAC AM1) and experimentally determined structures. The two remaining steps to the final product are very closely related to the known high yield conversion of the fluorenyl analog [$(C_6H_4)_2CH(OH)$] to the spiro-diketone product [$(C_6H_4)_2C(C(O)C_6H_4C(O)$] and to proceed similarly (7).

Figure 7B:
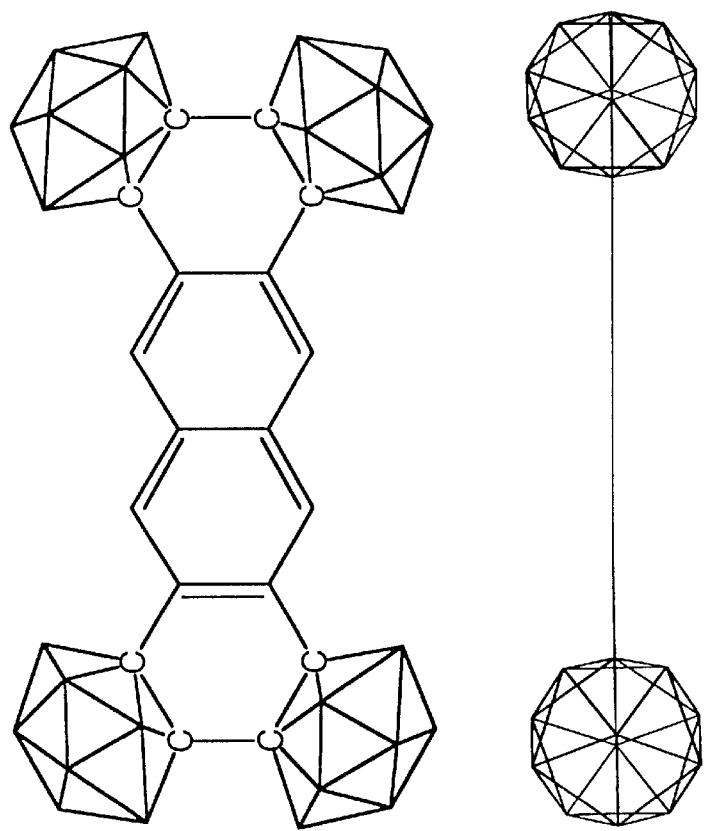
FIG. 7 represents two subunits for use in the construction of linear nanoscale arrays.
Figure 7A:
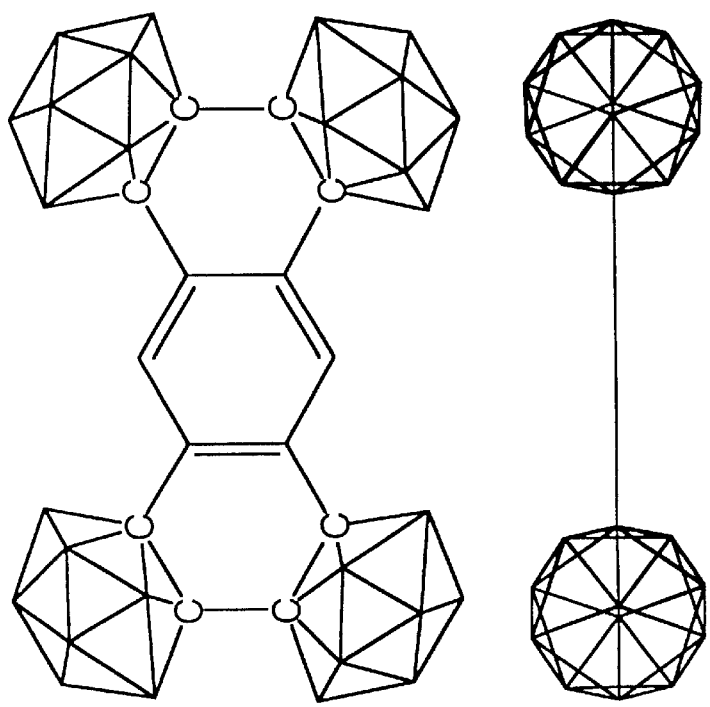

Solid Rings. Intermediates in the preparation of synthons A and B are the known dilithio- and di-Grignard-bis-cluster compounds (8), which may be reacted with essentially any appropriately substituted species to form a variety of bridged bis-cluster species, as illustrated in the synthesis shown in FIG. 3. In the case of synthon B, the linking unit has been modeled after an $SiO_2$-anthracene linked species. As mentioned above, the substituted arene may, however, be any of a very wide range of species, including polyfunctional, polycyclic, and polysubstituted species. A number of particularly interesting examples arise from such polysubstituted aromatic hydrocarbons with unique geometric arrangements. Several examples for the bis-cluster species are shown in FIG. 5, including the benzene (a), triphenylene (b), and coronene (c) polysubstituted aromatic species, with (d) demonstrating, more specifically, the nature of the bonding between the bis-cluster unit and the arene rings. The same arene π-system examples are shown with an alternative ortho-$C_2B_{10}H_{12}$ mono-cluster linkage in FIG. 6, where the same basic linkage approach between the cluster and the aromatic ring system is utilized by way of a tetrahedral bridging atom(d). The axes of the bis-cluster subunits, as in synthons A and B, are rigidly held perpendicular to the plane of the polycyclic aromatic ring systems. It should still be possible, however, to design the bridging assemblies such that electronic communication between the electron delocalized bis-cluster subunits and the delocalized aromatic hydrocarbon π-system can occur (as indicated by semiempirical calculations). This conjugation between the cage and arene π-systems may also be achieved, or even significantly enhanced, through the formation of species in which the two extra-bis linkage carbon atoms are joined directly to an arene ring, such as shown for two simple ortho-$C_2B_{10}H_{12}$-based model molecules in FIG. 7, where substituted benzene (a) and napthalene (b) structures are shown both perpendicular to (top) and parallel to (bottom) the planes of the aromatic rings, again with unlabeled cluster vertices being boron-hydrogen bonds and with all cluster-arene connections being made via carbon-carbon bonds. Compounds based upon structures like those shown in FIG. 7 may also be used to build larger arrays similar to those shown in FIG. 5. Consistent between all of the molecules in FIGS. 5 through 7, the full variety of aromatic ring species may be utilized in the design of novel synthons for specific structural and electronic applications. Molecular orbital calculations have shown that the electron delocalized clusters may be conjugated with the π-system of the linking arene, depending upon the identity of the linking unit and the geometry of the assembly. This feature should give rise to a number of interesting electronic properties in larger assemblies composed of these cage-arene conjugated systems (vide infra). Furthermore, the electronic properties of these units may be readily modified by changing the chemical attributes of the linking units. In the case of the arene species considered above, this modification of physical, chemical, and structural attributes is achieved by the substitution of anthracene, coronene, etc., for the simple benzene-based starting structures. Other modifications, such as the addition of electron withdrawing or donating groups, would also change the electronic properties of these selected aromatic ring systems.

Figure 8B:
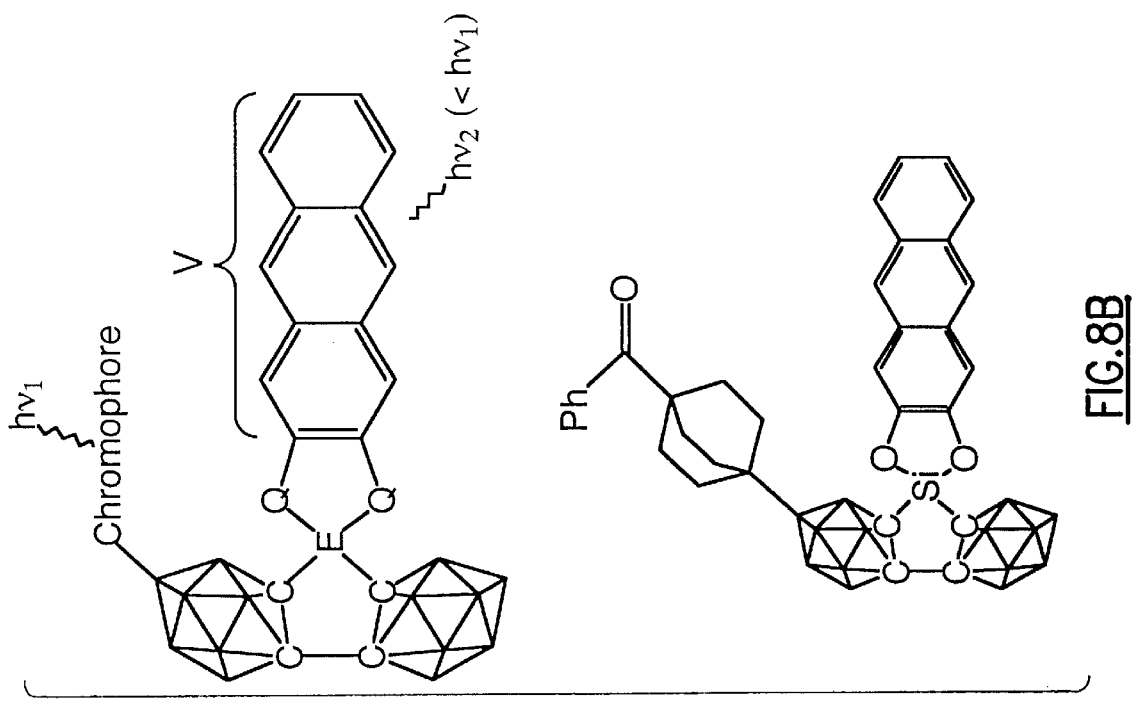
FIG. 8 demonstrates two characterization approaches for the examination of electronic properties in the synthons of the present invention.
Figure 8A:
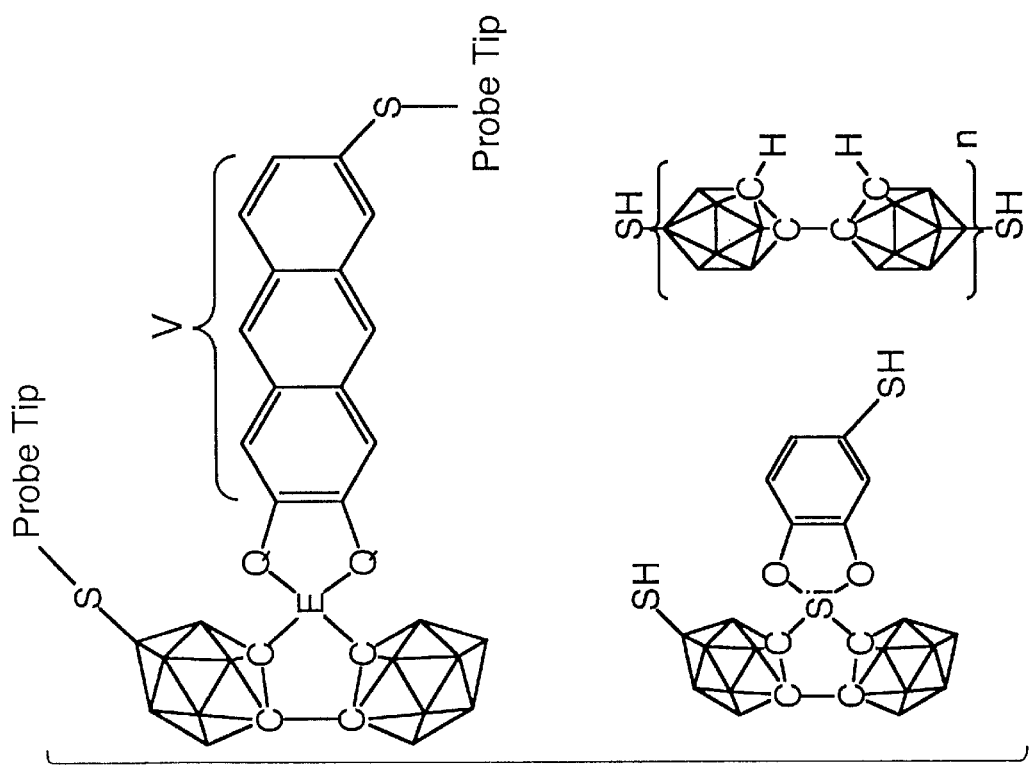

The extent of the electronic and energy transfer interactions between the polyhedral cages and the pendent groups (i.e., arenes) may be explored with model compounds using such spectroscopic and electronic property techniques as break juncture probing, fluorescence probe photochemical measurements, and NMR studies. The use of the break juncture probe and fluorescence probe techniques for the measurement of the electronic communication and energy transfer between the electron delocalized bis-cluster subunits and the delocalized aromatic hydrocarbon π-system for a selection of model compounds proposed for study are summarized in FIG. 8. Break juncture techniques (a) involve the formation of molecular-based electronic circuits between two atom-sized tips of a stress-fractured gold surface. Mounted to the gold surface by sulfur linkages, the electronic properties of the examined molecules, including molecular resistivity and capacitance, can be studied in great detail. Fluorescence probe techniques (b) involve the examination of the emission of light from one molecular fragment due to the absorption of light by another molecular fragment, examining the nature of the coupling of these two fragments in the same molecule, thereby providing insights into the degree of cross-molecule communication. Derivatives of the compounds shown in FIG. 7 may also be studied with the break juncture techniques.

Figure 9:
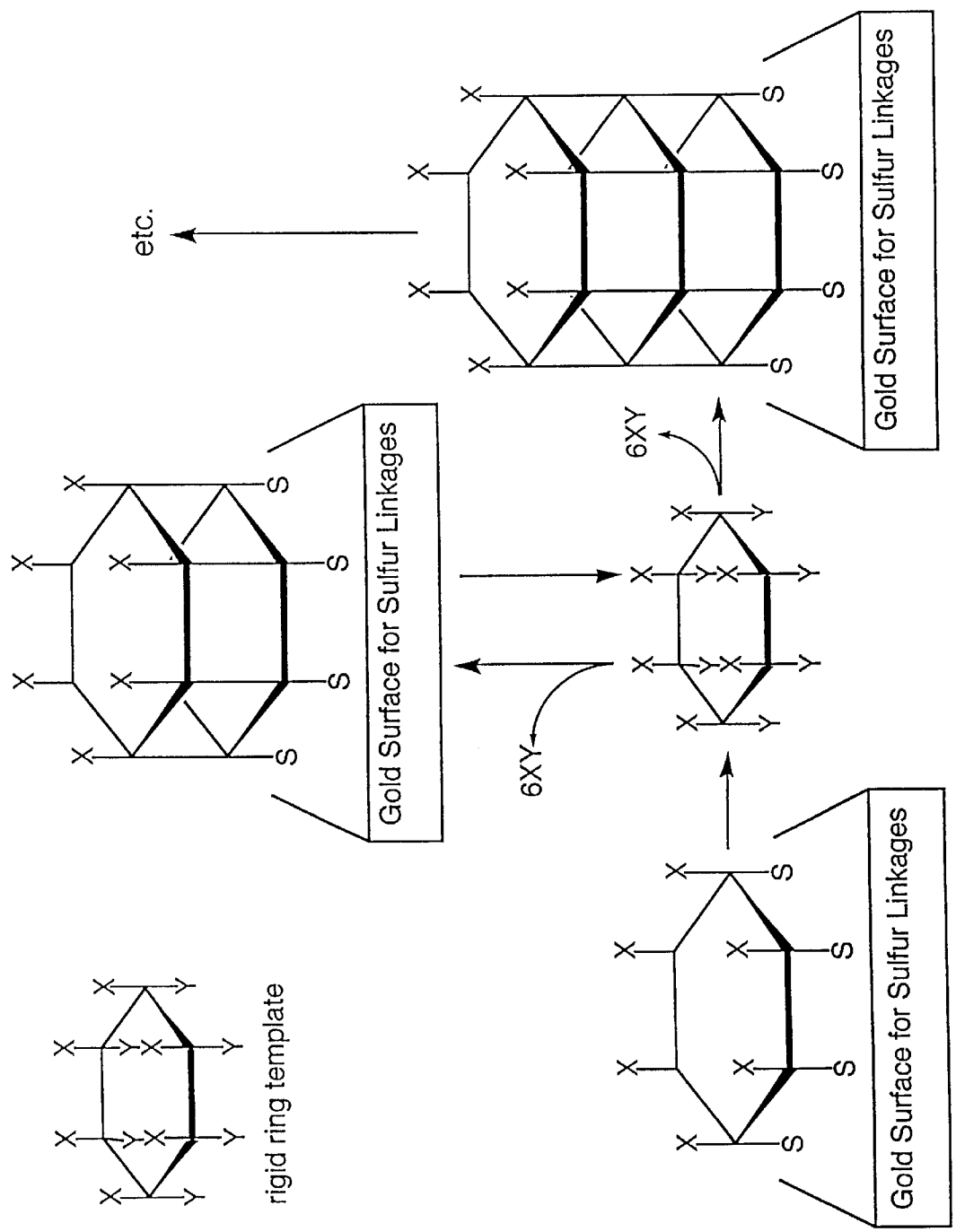
FIG. 9 is a schematic representing an approach for engineering stacked rigid rods from the synthons of the present invention.

Columns, Rods and Chain Structures. The synthesis of larger macrostructural assemblies requiring different functional groups on opposite sides of ring systems for the purpose of unidirectional coupling of the rings to one another presents an interesting but synthetically tractable challenge. The goal is to design a synthetic scheme that leads only to the desired isomer (i.e., all cis- derivatization relative to the ring) without side products or other substitution patterns. In an "undirected" synthesis, numerous isomers may be possible with separation problems and the concomitant poor overall yield of the desired species would render the approach prohibitive. It may, however, be possible to design synthetic schemes in which functionalization occurs entirely regiospecifically. One such approach is summarized in FIG. 9 in which a metal surface, such as gold, could be employed to bind functional groups to only one "face" of a starting ring system, as demonstrated by the use of sulfur atoms, leading to the gold surface-directed derivatization of an all cis-functionalized, multiple bis-cluster species. This then leaves the upper "face" of the system free for unhindered chemical derivatization. In FIG. 9, the hexameric species diagramed at top left is representative of any rigid ring-based structure with the appropriate linking groups X and Y. Once the derivatization has been completed, the ring assembly can be displaced from the surface by several means, such as by employing a stronger organometallic ligand or an overpressure of a gaseous ligand (e.g., CO). The resulting ring would be in the desired configuration with a "locked" all cis-, differentially-functionalized substitution pattern. This approach of using a metal to block chemical access to specific regions of a substrate molecule is frequently employed with great success in organometallic catalytic reactions.

Figure 10:
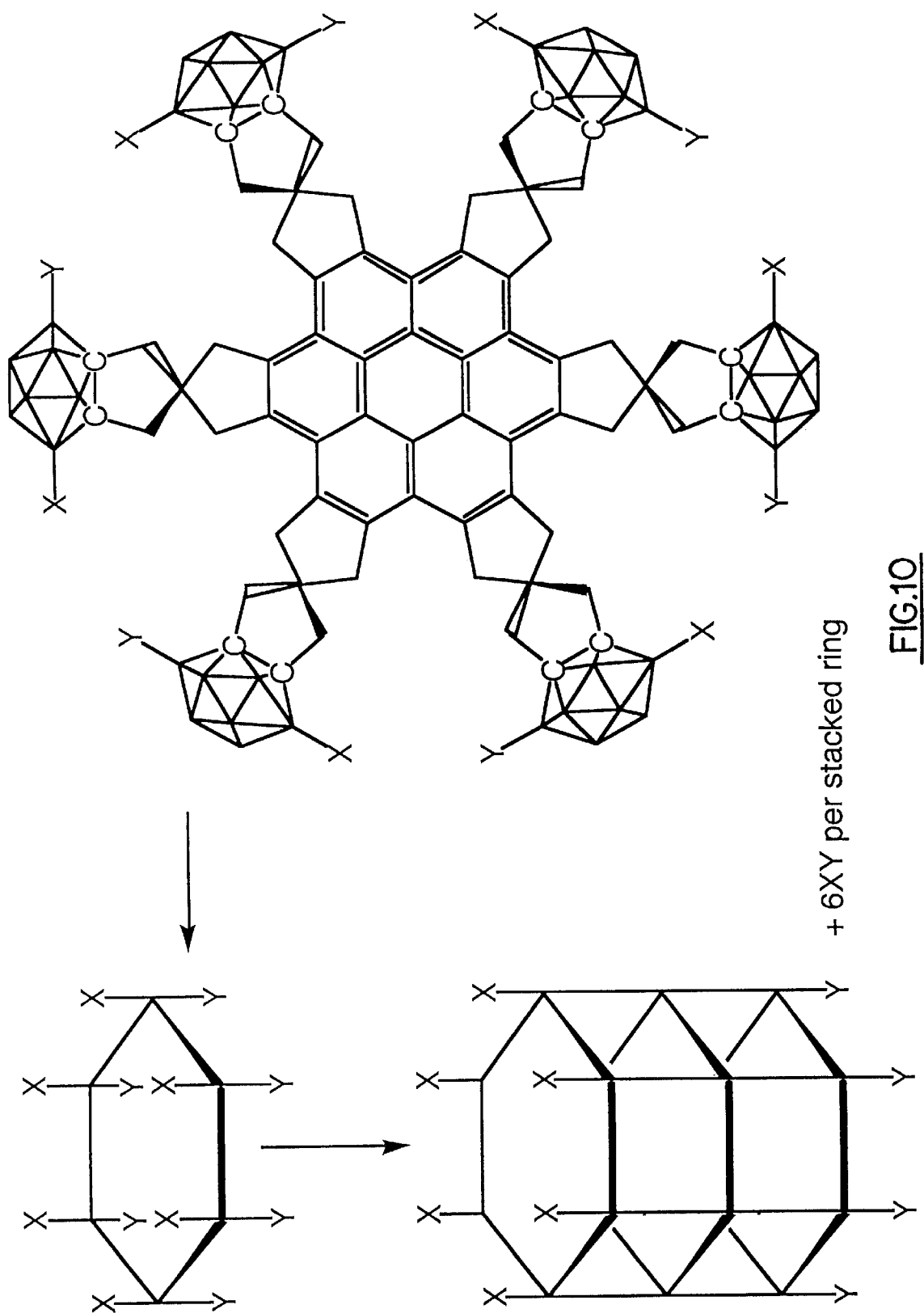
FIG. 10 demonstrates a specific rigid rod subunit based on a mono-cluster species and the subsequent stacking of that species.

It should be readily possible to stack larger assembly units to form even larger arrays as described in FIG. 9 through rather straightforward chemical linking techniques facilitated by π-stacking interactions. One example, which is based upon hexameric ortho-$C_2B_{10}H_{12}$-linked coronene units, is shown in FIG. 10. The number of ortho-$C_2B_{10}H_{12}$ "columns" may be varied by choice of different arene units while the interlayer spacing may be modified by using different linear linking groups (i.e., alkynes, para-$C_2B_{10}H_{12}$, etc.). An interesting feature observed in the calculated optimized structure for the stacked structure in FIG. 10 is a slight rotation of successive units to yield a shallow "screw-like" overall arrangement of the rod. Other interlayer connectors and arene subunits are possible in which this relative rotation is not observed in the optimized structure.

Figure 11:
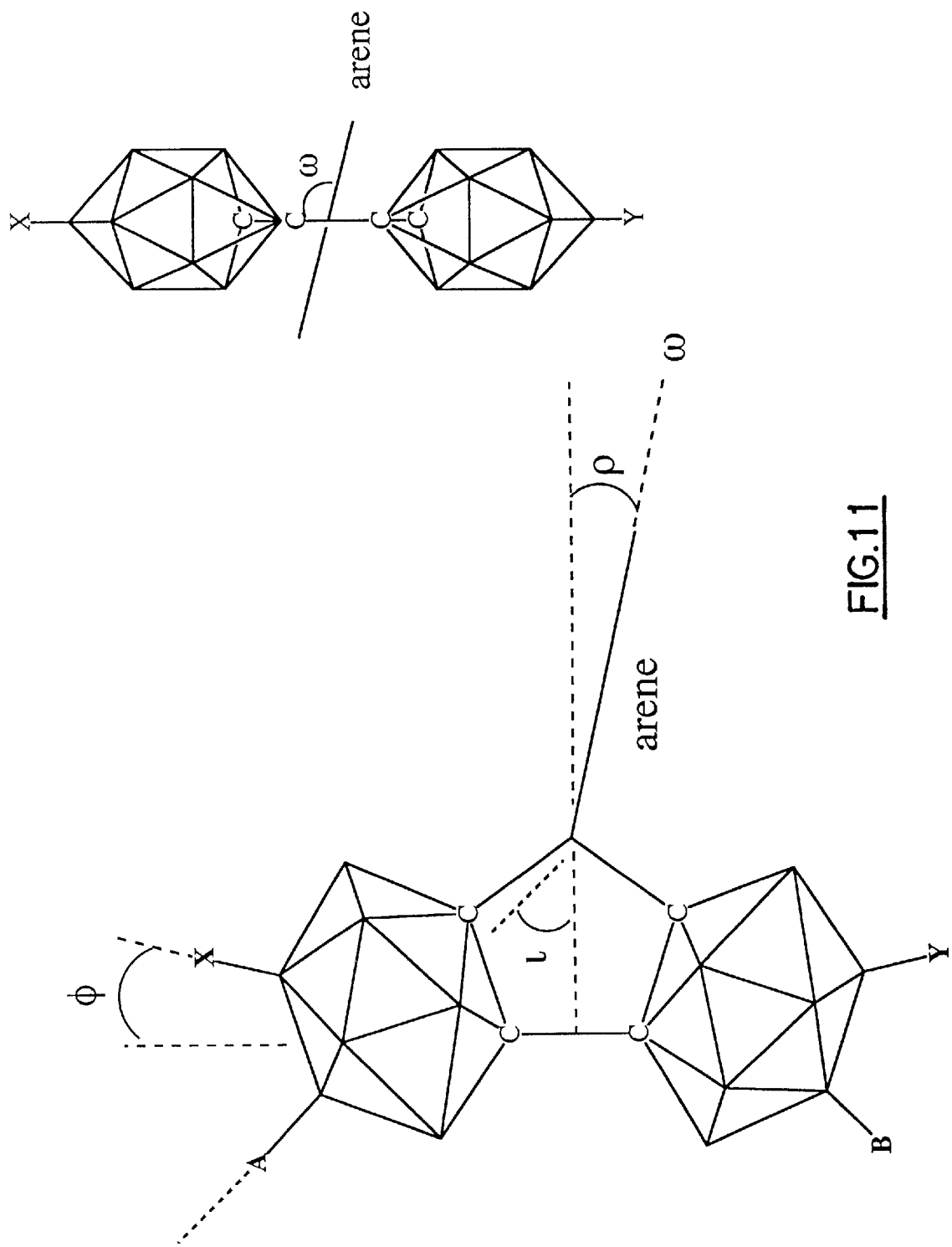
FIG. 11 depicts the four angles, $\Phi$, $\iota$, $\rho$ and $\omega$, essential in the construction of molecular assemblies based upon the synthon of the present invention.

In the synthons such as those shown in FIGS. 1 and 2, several critical angles and interatomic distances define a rigid structural unit capable of assembly into precisely defined larger macrostructural systems. These structural elements are more carefully defined in FIG. 11, where the structural features directing macrostructural assembly of synthons into larger units are specified. The various angles ($\Phi$, $\iota$, $\rho$, $\omega$) and distances may be readily modified through substitutional and compositional control of the subunits, especially by changing the extra-bis-linkage atom connecting the cluster units and by modifying the arene and its mode of connection to the bridge atom (vide infra).

Figure 12:
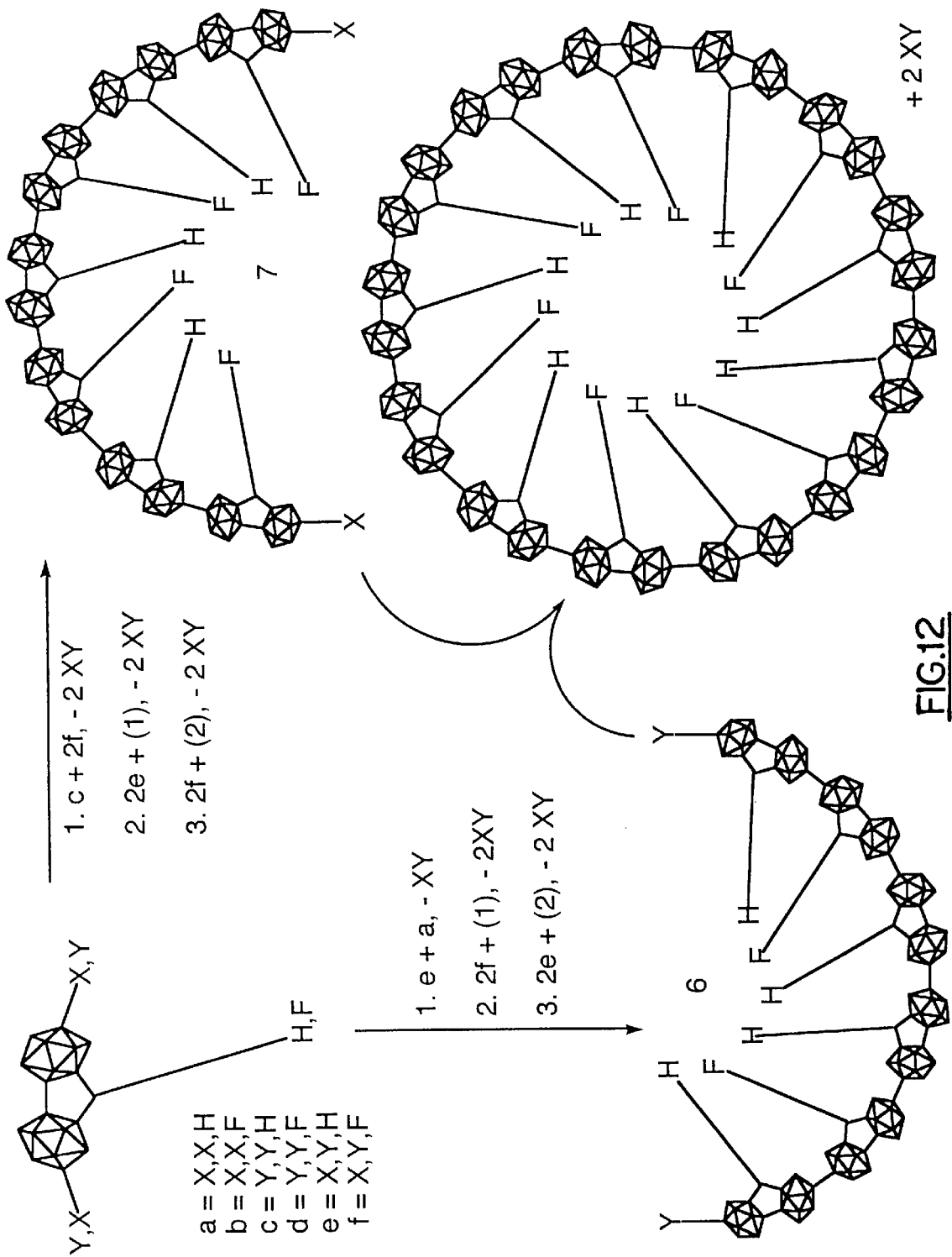
FIG. 12 demonstrates the synthesis of a 13-member ring structure from an idealized synthon of the present invention.
Figure 13:
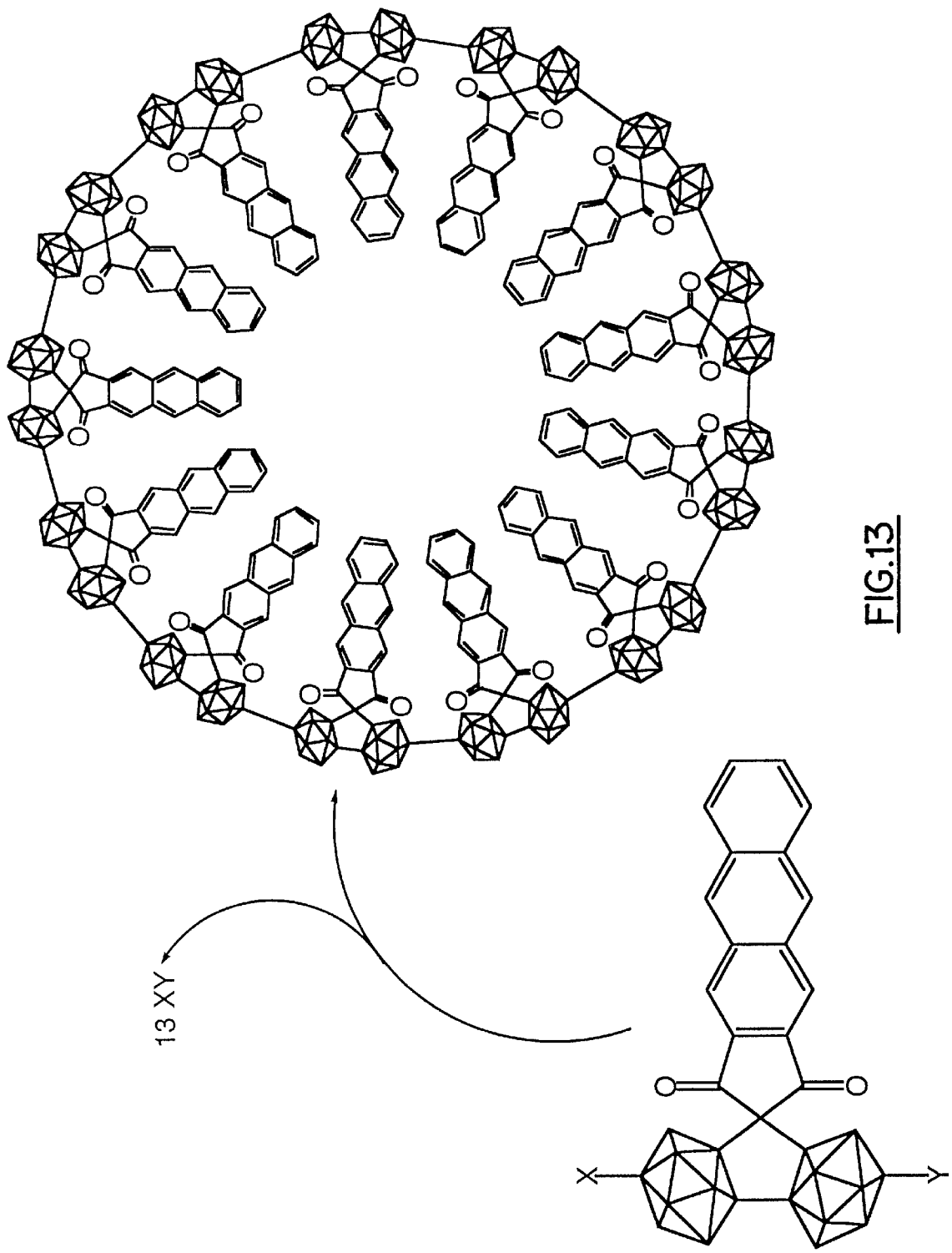
FIG. 13 represents a 13-member ring structure from a specific variant of the synthons described in the present invention.

Open Rings. Another "prefabricated" macromolecular form required for the fabrication of more complex nanosystems is the ring. A variety of ring structures of varying sizes and components are possible using the rigid functionalized building blocks embodied in the synthons previously described. For example, in the case of the use of synthon A, coupling of bis-cluster subunits at positions X and Y (FIG. 11) would yield an essentially strain-free, rigidly planar ring system composed of twelve to sixteen subunits, as shown in FIG. 12, where a convergent synthetic scheme for the macrostructural metathesis of one such ring, a thirteen-subunit A-type ring system, is described. A specific example of this approach for a B-type synthon is provided in FIG. 13.

Figure 14:
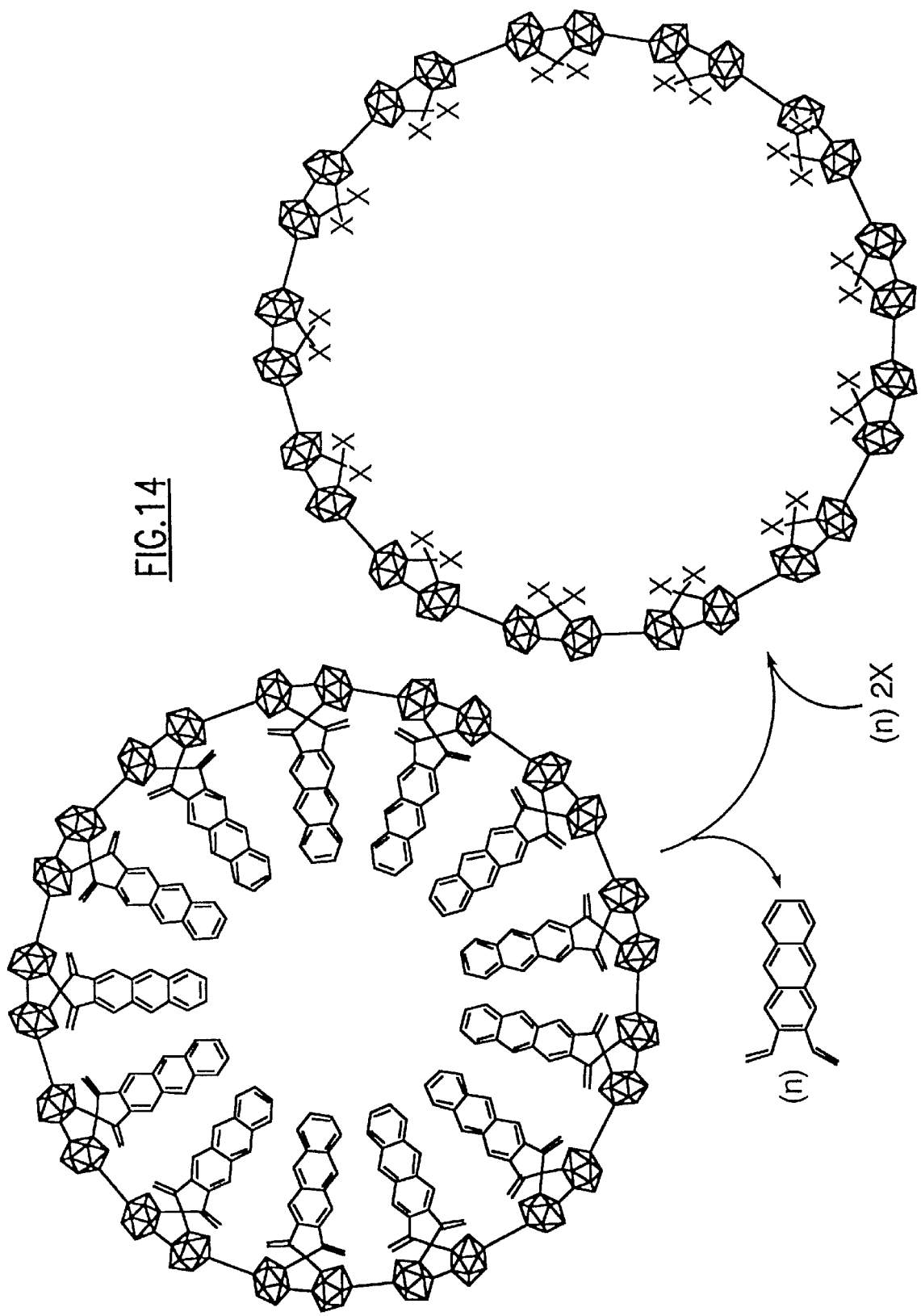
FIG. 14 details an internal arene cleavage for the formation of ring cavities from the 13-member rings proposed in FIGS. 12 and 13.

An important feature driving the unidirectional metathetical synthesis (FIG. 12) is the significant stabilization gained through the π-stacking of the internal arene rings. This π-stacking may also be greatly enhanced through the alternation of "normal" (hydrogen-substituted) arene and perfluorinated arene units. This alternation of perfluorinated with hydrogen-substituted arene synthons can be readily optimized to provide both a significant driving force (calculated at ca. 130 Kcal/mol for a thirteen subunit ring) and synthetic directional control ("template-like" synthesis) for the reactions shown in FIG. 12. Several features of the rings, such as the examples shown in FIGS. 12 and 13, deserve further note. The circular track size of the ring can be readily adjusted from ca. 36 Å (4 membered ring) to 118 Å (13 membered rings) and well beyond with larger linkers or spacers (i.e., para-$C_2B_{10}H_{12}$, alkyne, phenyl, etc.) between each synthon or through the incorporation of additional synthon units. In addition, different synthons produce rings of different sizes. Because of the rigid properties of the component synthon units and the significant stabilization added by the arrangement of the π-systems along the inside of the ring, the ring is constrained to be planar. Changes in the method of linking the subunits together (i.e., para-$C_2B_{10}H_{12}$, alkyne, phenyl, etc.) change the size of the central hole. It should also be possible to cleave off the inward arene "spokes" of the ring through literature reactions as illustrated in FIG. 14, where (n) is the number of inter-ring molecular fragments, equal to the number of synthons. Finally, as seen later in more complex assemblies, variations in the arene components of adjacent synthons in the ring lead to precise overall control of the geometry of the central cavity of the ring, allowing design of interfitting components.

Figure 15:
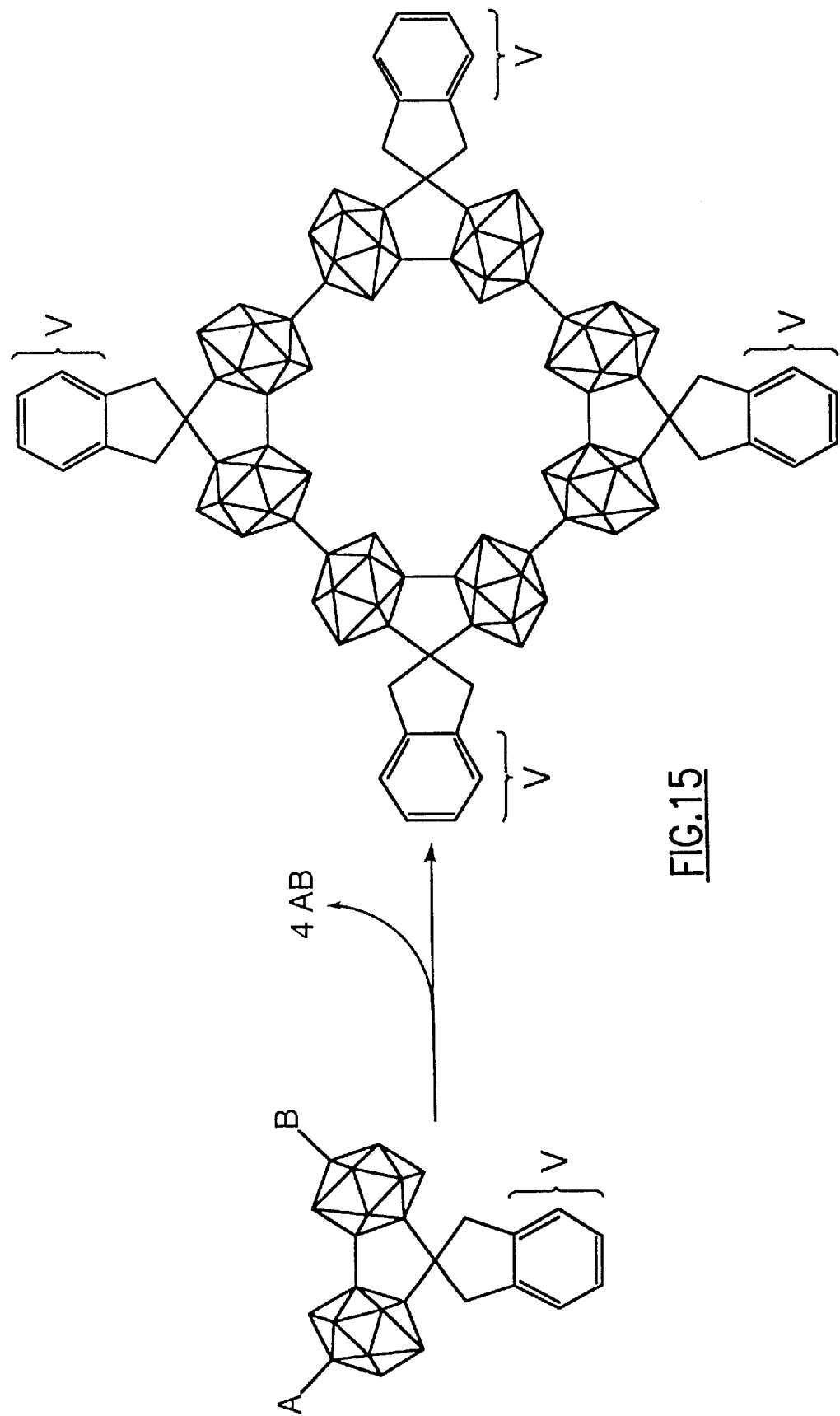
FIG. 15 represents a variant on the ring formation process from the functionalization of two alternative positions of the synthons of the present invention.

If the subunit linking were to occur at cage positions A and B instead of linking the synthon subunits at the X and Y cage positions (FIG. 11), then an "inverted" ring system would be obtained in which the arene units are arrayed on the outside of the polyhedral ring system. An example of such an inverted system is shown in FIG. 15. It would be expected that the control of the sizes and geometries of these "inverted" rings would be similar to that described above for the "normal" ring systems.

Figure 16:
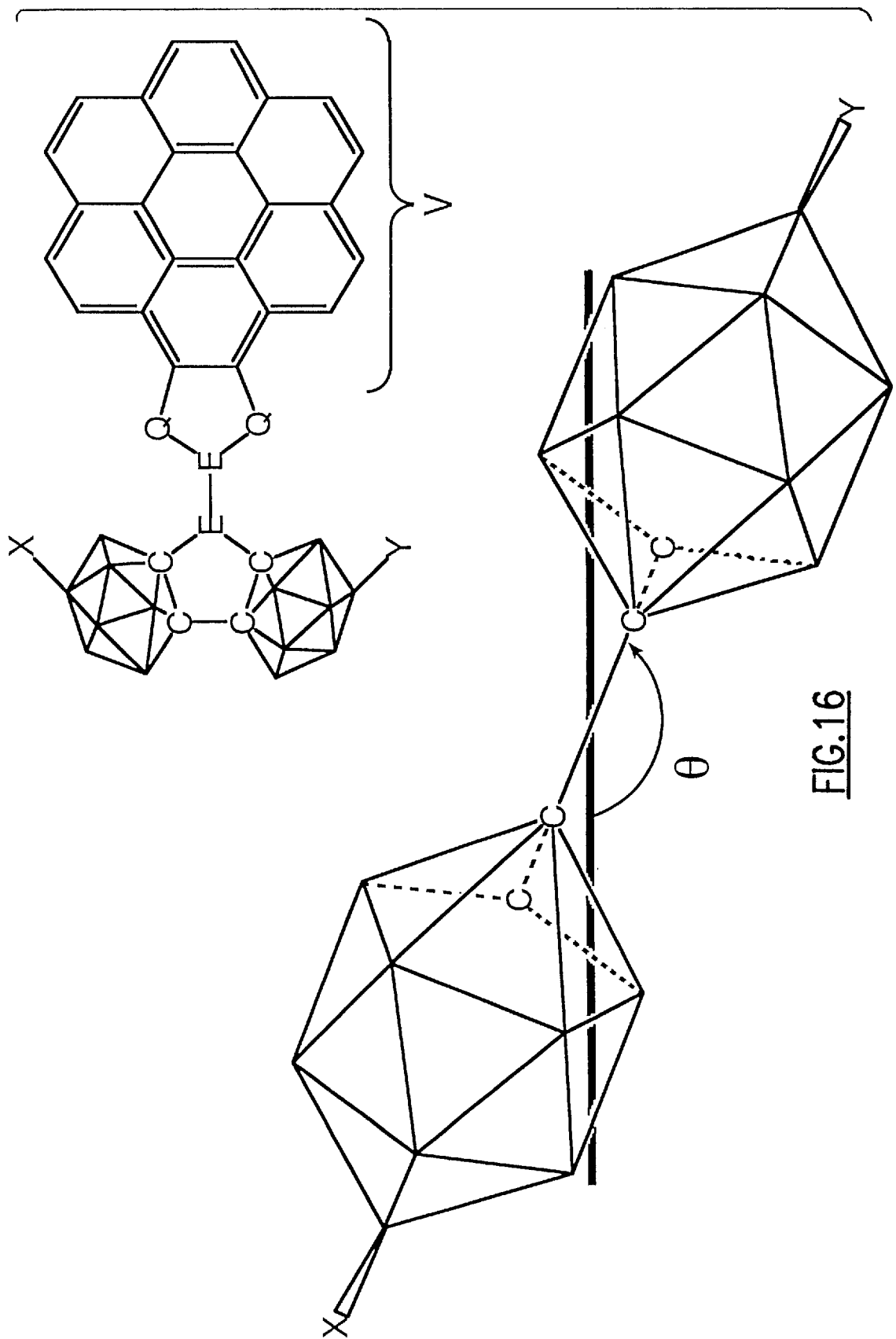
FIG. 16 details the modifications required to design synthons capable of the structural flexibility necessary for the formation of helical structures.

Helices. In the ring structures described in the previous section, it can be seen that, through simple modifications to the arene unit and the inter-synthon linking, helical rather that planar structures may be developed. This helical formation is easily accomplished by, for example, using a variety of arenes (such as coronene) linked through a B-B bridge, or any other selection of E which provides for a single bond between the bis-cluster and arene fragments (FIG. 2). These helices, and especially the double helices discussed in the next section, have direct and profound applicability to such diverse technology areas as molecular computing and high tensile materials. A typical synthon for formation of these proposed helical structures is provided in FIG. 16, where E is any one of many possible linking atoms or molecular fragments. Of important note in this FIG. is the referenced angle made between the plane of the π-system and the bis-cluster backbone itself, where the size of this angle determines the degree of curvature in the final helix. This structural property, like the many structural properties demonstrated in FIG. 11 and in the considerations of variable linkage groups between the bis-cluster subunit and the π-system, is highly variable, able to be easily customized for a desired value based on the aromatic species, linking group between bis-cluster and π-system, the nature of the synthon spacer in the formation of the helix, etc. FIG. 17 provides some simple diagrams demonstrating the nature of the π-stacking interaction used to initially form and subsequently stabilize the synthon helix. Of particular note is the orientation of the stacked coronene species as shown in FIGS. 17a and b. FIG. 17c provides a simplified view of the actual spiraling result as observed from computational studies of the electrostatic stability arising from the stacking of the coronenes.

Figure 18:
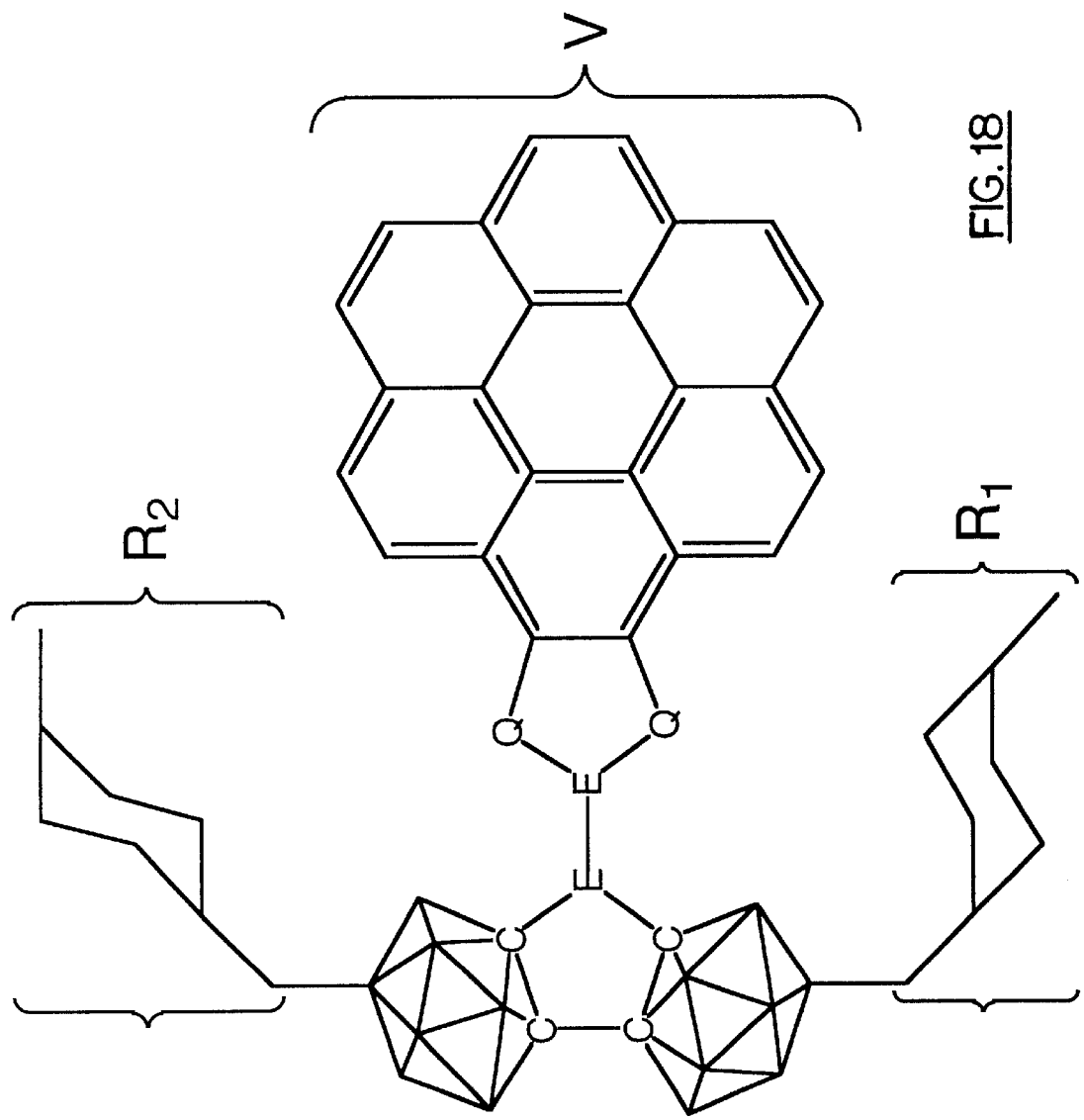
FIG. 18 describes the modifications made to the synthon of the present invention necessary for the formation of double helical structures.
Figure 19:
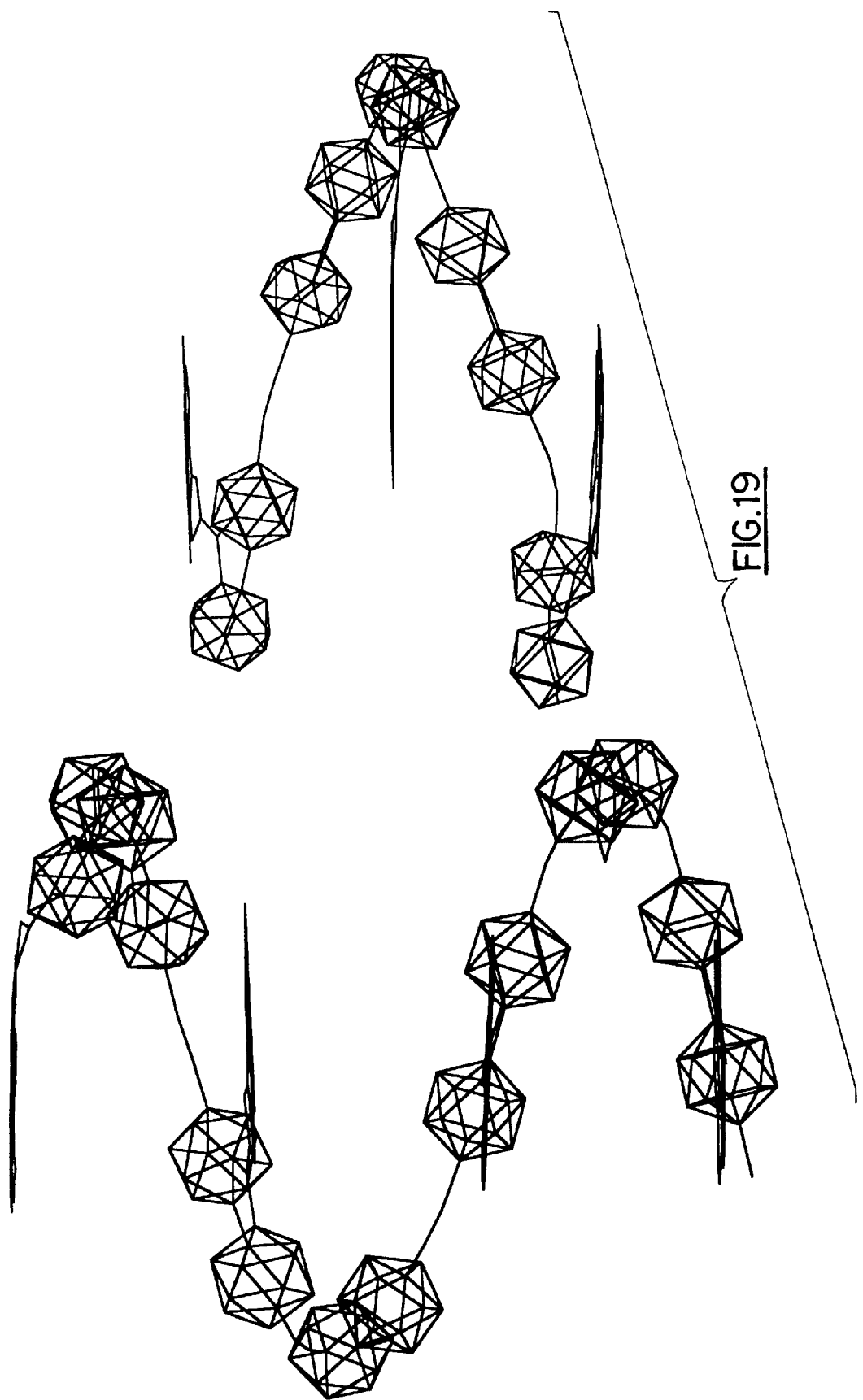
FIG. 19 depicts two fragmented segments of an idealized double helical structure from the synthons of the present invention.
Figure 20:
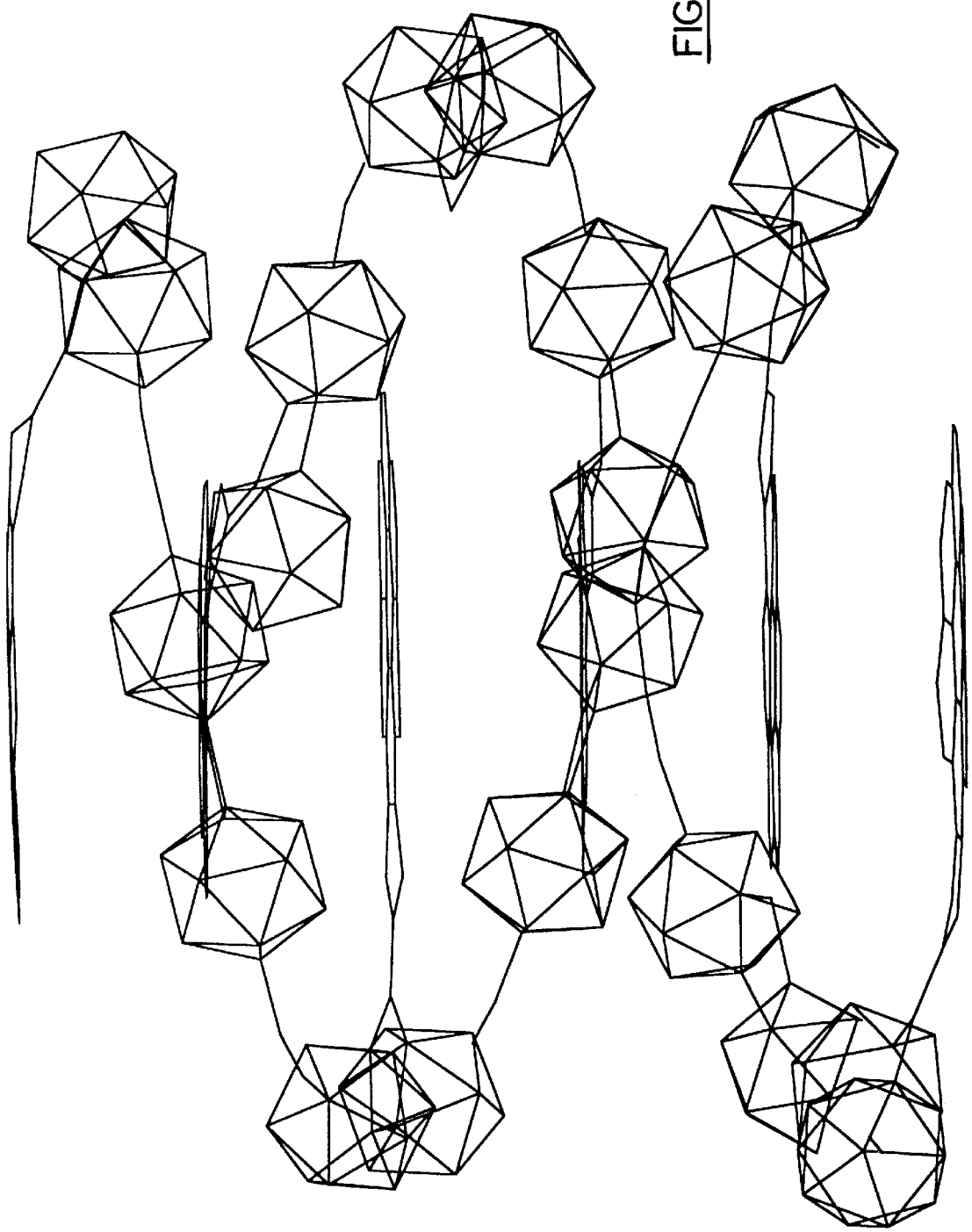
FIG. 20 depicts an idealized double helix from chemical calculations of a selected synthon of the present invention.

Double Helices. While the helical structures described above are expected to be very stable architectures, it should be possible to design and prepare more complex double helical structures, somewhat resembling DNA in overall form. The basic structural requirements for a synthon designed for the formation of double helices is outlined with FIG. 18, where the location and nature of the additional molecular fragments required to provide spacing within the double helix (R1, R2) are shown in the same coronene-based synthon described in FIG. 16. FIG. 19 shows the two molecular fragments of a proposed double helix structure separated from one another after a computational optimization of the stacking structure. FIG. 20 shows a computationally optimized model of the unfragmented, proposed double helical structure.

More Complex Structures Built from Simpler Macromolecular Subunits. By combining the "prefabricated" simpler units described above (e.g., rings, rods, helices, etc.), more complex structures may be built up, ultimately leading to the fabrication of nanoscale machines and assemblies.

The following comprises the various units suitable for use in fabricating the molecular nanosystems of the present invention.

GROUPINGS

Rigid Subunits (1) Polyhedral structures including boranes (e.g., arachno-$[B_3H_8]^{-1}$, nido-$B_5H_9$, nido-$B_{10}H_{14}$, closo-$[B_6H_6]^{-2}$, closo-$[B_{10}B_{10}]^{-2}$, conjuncto-$B_{20}H_{16}$, nido-$B_{10}H_{14}$, and related structures), carboranes (closo-$H_2C_2B_{10}H_{10}$, nido-$C_2B_4H_6$, nido-$C_2B_9H_{11}$, closo-$H_2C_2B_8H_8$, and related structures), Zintyl species (e.g., $[Bi_9]^{5+}$, $[Ge_9]^{2-}$, $[Bi_5]^{3+}$, $[Pb_5]^{2-}$, $[Sn_5]^{2-}$ clusters), and organometallic structures (e.g., $[Ni_4(tBuNC)_7]$, $[Fe_4S_4(NO)_4]$, $[Os_6H_2(CO)_{18}]$, $[M_4H_4(CO)_{12}]$, (where M=Re or Ru), $H_4M_4(CO)_{12}$ (where M=Os or Ru $[Os_3(CO)_{12}]$, and related structures).

(2) Organic Aromatic Structures (e.g., monocyclic hydrocarbons [benzene, cyclopropane, cyclobutane, and related structures], polycyclic hydrocarbons [naphthalene, anthracene, coronene, and related structures]).

(3) Organic three-dimensional rigid units (e.g., adamantane-based structures, para-cyclophane-based structures, norbornane-based structures, calaxyrene-based structures, and related rigid structures).

Connecting Assemblies (1) Polyhedral structures including boranes (e.g., arachno-$[B_3H_8]^{-1}$, nido-$B_5H_9$, nido-$B_{10}H_{14}$, closo-$[B_6H_6]^{-2}$, closo-$[B_{10}B_{10}]^{-2}$, conjuncto-$B_{20}H_{16}$, nido-$B_{10}H_{14}$, conjuncto-$B_{18}H_{22}$, and related structures), carboranes (closo-$H_2C_2B_{10}H_{10}$, nido-$C_2B_4H_6$, nido-$C_2B_9H_{11}$, closo-$H_2C_2B_8H_{12}$, and related structures), Zintyl species (e.g., $[Bi_9]^{5+}$, $[Ge_9]^{2-}$, $[Bi_5]^{3+}$, $[Pb_5]^{2-}$, $[Sn_5]^{2-}$ clusters), and organometallic structures (e.g., $[Ni_4(tBuNC)_7]$, $[Fe_4S_4(NO)_4]$, $[Os_6H_2(CO)_{18}]$, $[M_4H_4(CO)_{12}]$, (where M=Re or Ru), $H_4M_4(CO)_{12}$ (where M=Os or Ru) and $[Os_3(CO)_{12}]$, and related structures).

(2) Organic Aromatic Structures (e.g., monocyclic hydrocarbons [benzene, cyclopropane, cyclobutane, and related structures], polycyclic hydrocarbons [naphthalene, anthracene, coronene, and related structures]).

(3) Organic functional groups (e.g., alkynes, alkenes, esters and similar groups).

While the present invention has been particularly shown and described with reference to the preferred mode as illustrated in the drawings, it will be understood by one skilled in the art that various changes in detail may be effected therein without departing from the spirit and scope of the invention as defined by the claims.

References (1) Inorg. Chem. 1973, 12, 708.
(2) Drexler, K. Eric. Nanosystems: Molecular Machinery, Manufacturing, and Computation. New York: John Wiley and Sons, Inc. 1992.
(3) Heying, T. L. Prog. Boron Chem. 1970, 2, 119.
(4) Steudel, R. Chemistry of the Non-Metals deGruyter: Berlin, 1977.
(5) Barnett-Thamattoor; Zheng, G.; Ho, D. M.; Jones, M., Jr. Inorg. Chem. 1996, 35, 7311.
(6) Grimes, R. N. Carboranes; Academic: New York, 1970.
(7) Synthesis Communications, 1987 (10), pg. 915
(8) Greenwood, N. N.; Earnshaw, a. Chemistry of the Elements Pergamon Press, Oxford, 1985.

We claim:

1. A molecular synthon for the fabrication of larger molecular structures which comprises;

(a) one or more main group polyhedral clusters and
   (b) a second molecular framework covalently linked to the main group polyhedral cluster(s).

2. The synthon of claim 1 in which the main group polyhedral cluster(s) is at least one selected from the group consisting of boranes, and other heteroboranes.

3. The synthon of claim 1 in which the second molecular framework through which to introduce either covalent bonding or electrostatic connectivity between synthons is at least one selected from the group consisting of main groups boranes, carboranes, other heteroboranes, and organic structures, including monocyclic hydrocarbons, polycyclic hydrocarbons, and organic functional groups.

4. The synthon of claim 1 in which the larger structures fabricated from the molecular synthons are assembled through the covalent attachment of the main group polyhedral frameworks to one another as to form a connected molecular scaffolding for the larger structures.

5. The synthon of claim 1 in which the larger structures fabricated from the molecular synthons are assembled by way of the second molecular framework through the use of covalent bonding or electrostatic interactions between these second molecular frameworks.

6. The synthon of claim 1 in which the second molecular framework provides for stability between synthons by way of connectivity between these second molecular frameworks either through the covalent and/or electrostatic attachment of these molecular frameworks to one another after their covalent attachment to the polyhedral cluster(s) or through their covalent and/or electrostatic attachment to one another prior to the covalent attachment of the polyhedral cluster(s).

7. The synthon of claim 1 in which the molecular synthons form extended arrays of connected synthons of indefinite synthon number through the covalent attachment of the polyhedral clusters to one another and either the covalent attachment to or electrostatic stabilization between the second molecular frameworks with said extended arrays of indefinite synthon number include at least one selected from the group consisting of helical structures, linear arrays, rod structures, two-dimensional extended arrays, and three-dimensional extended arrays.

8. The synthon of claim 1 in which the molecular synthons form discrete macromolecular structures or nanoscale assemblies through the covalent attachment of the polyhedral clusters to one another and either the covalent attachment to or electrostatic interactions between the second molecular frameworks with said discrete structures include at least one selected from the group consisting of ring structures, helical structures, linear structures, rod structures, two-dimensional discrete assemblies, and three-dimensional discrete assemblies.

* * * * *